United States Patent
Bäck

(10) Patent No.: US 8,764,926 B2
(45) Date of Patent: Jul. 1, 2014

(54) METHOD AND APPARATUS FOR MANUFACTURING ELASTICATED WEBS COMPRISING DISCONTINUOUS ELASTIC THREADS

(75) Inventor: Lucas Bäck, Billdal (SE)

(73) Assignee: SCA Hygiene Products AB, Gothenburg (SE)

(*) Notice: Subject to any disclaimer, the term of this patent is extended or adjusted under 35 U.S.C. 154(b) by 312 days.

(21) Appl. No.: 13/318,055

(22) PCT Filed: Apr. 22, 2010

(86) PCT No.: PCT/SE2010/050445
§ 371 (c)(1),
(2), (4) Date: Nov. 15, 2011

(87) PCT Pub. No.: WO2010/126431
PCT Pub. Date: Nov. 4, 2010

(65) Prior Publication Data
US 2012/0055615 A1    Mar. 8, 2012

(30) Foreign Application Priority Data
Apr. 30, 2009   (WO) ................ PCT/SE2009/050468

(51) Int. Cl.
*A61F 13/15* (2006.01)

(52) U.S. Cl.
CPC ..... *A61F 13/15601* (2013.01); *A61F 13/15609* (2013.01); *A61F 13/15804* (2013.01)
USPC ........... 156/177; 156/179; 156/181; 156/267; 156/440

(58) Field of Classification Search
None
See application file for complete search history.

(56) References Cited

U.S. PATENT DOCUMENTS

| 4,379,016 A |   | 4/1983  | Stemmler et al.        |
|-------------|---|---------|------------------------|
| 4,578,133 A |   | 3/1986  | Oshefsky et al.        |
| 4,675,068 A |   | 6/1987  | Lundmark               |
| 4,786,346 A |   | 11/1988 | Ales et al.            |
| 4,813,946 A |   | 3/1989  | Sabee                  |
| 5,643,396 A |   | 7/1997  | Rajala et al.          |
| 5,660,657 A |   | 8/1997  | Rajala et al.          |
| 5,660,664 A | * | 8/1997  | Herrmann ....... 156/161|
| 6,179,946 B1|   | 1/2001  | Ward et al.            |
| 6,482,278 B1|   | 11/2002 | McCabe et al.          |
| 6,521,320 B2|   | 2/2003  | McCabe et al.          |

(Continued)

FOREIGN PATENT DOCUMENTS

| CN | 1319384 A   | 10/2001 |
|----|-------------|---------|
| JP | 2006-519666 | 8/2006  |

(Continued)

OTHER PUBLICATIONS

Office Action issued by the Russian Patent Office in Russian patent application No. 2011148587 dated Apr. 3, 2013 (and English translation thereof) (22 pages).

(Continued)

*Primary Examiner* — Barbara J Musser
(74) *Attorney, Agent, or Firm* — Drinker Biddle & Reath LLP

(57) ABSTRACT

A method for manufacturing elasticated webs including discontinuous elastic threads, and methods for manufacturing articles from such elasticated webs. Apparatus for carrying out the methods. Further, elasticated webs and articles which can be manufactured using the methods.

17 Claims, 14 Drawing Sheets

(56) References Cited

U.S. PATENT DOCUMENTS

| | | |
|---|---|---|
| 6,551,431 B2 | 4/2003 | Lee |
| 6,623,468 B2 | 9/2003 | Shimoe |
| 2002/0193775 A1 | 12/2002 | Shimoe |
| 2003/0077008 A1 | 4/2003 | Plourde et al. |
| 2005/0000628 A1 | 1/2005 | Norrby |
| 2006/0064069 A1 | 3/2006 | Rajala et al. |
| 2006/0243373 A1 | 11/2006 | Krueger et al. |

FOREIGN PATENT DOCUMENTS

| | | |
|---|---|---|
| JP | 2007-044295 | 2/2007 |
| WO | 97/00654 | 1/1997 |
| WO | 98/25767 | 6/1998 |
| WO | WO 2004/078083 | 9/2004 |
| WO | 2009/002235 | 12/2008 |

OTHER PUBLICATIONS

English translation of Japanese Office Action mailed May 21, 2013 in Japanese patent application No. 2012-508423 (3 pages).

Search Report issued Jun. 20, 2013 in Chinese patent application No. 200980160182.6 (and English translation thereof) (14 pages).

\* cited by examiner

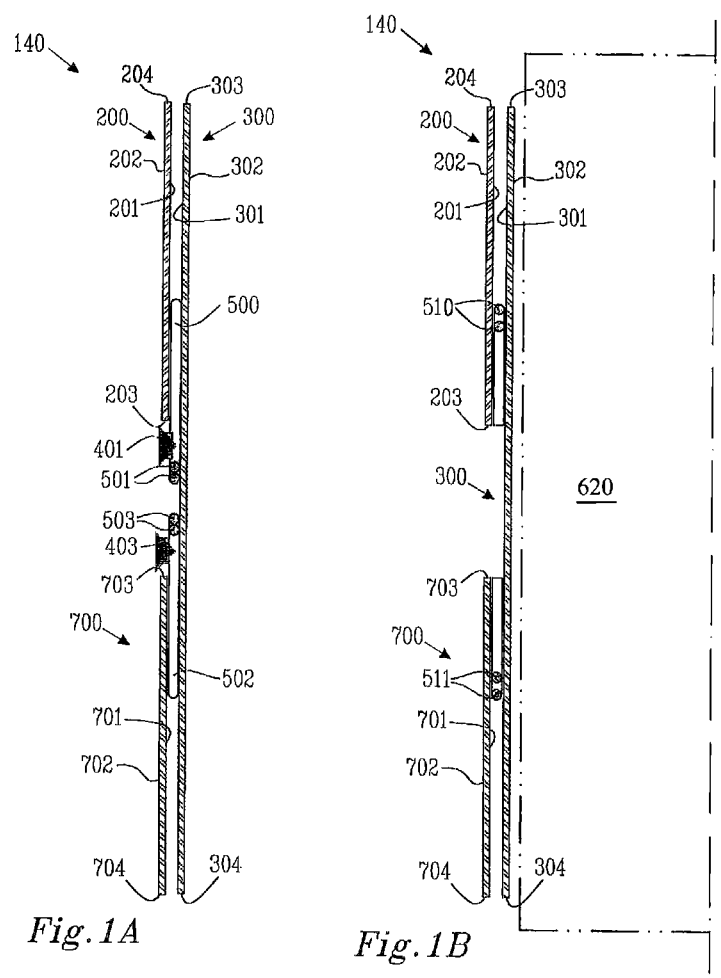

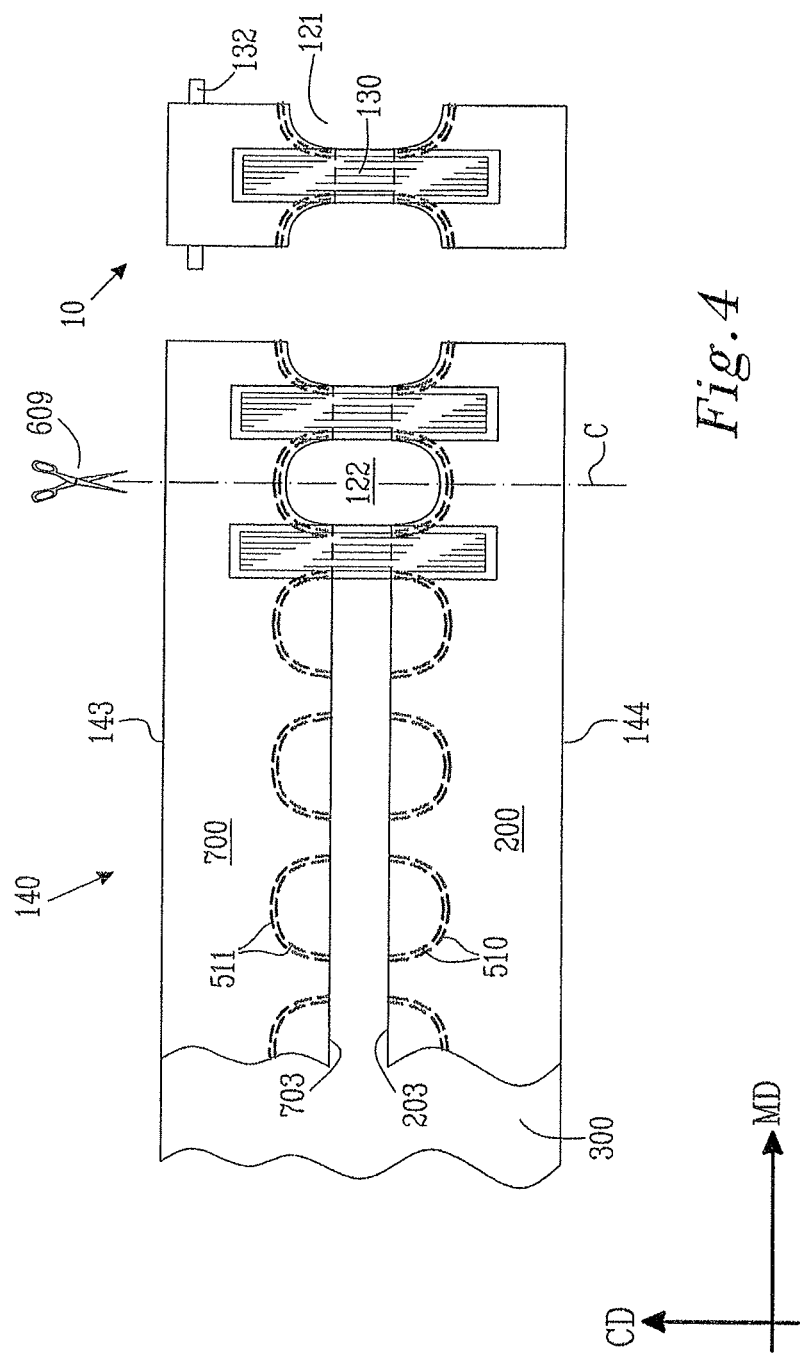

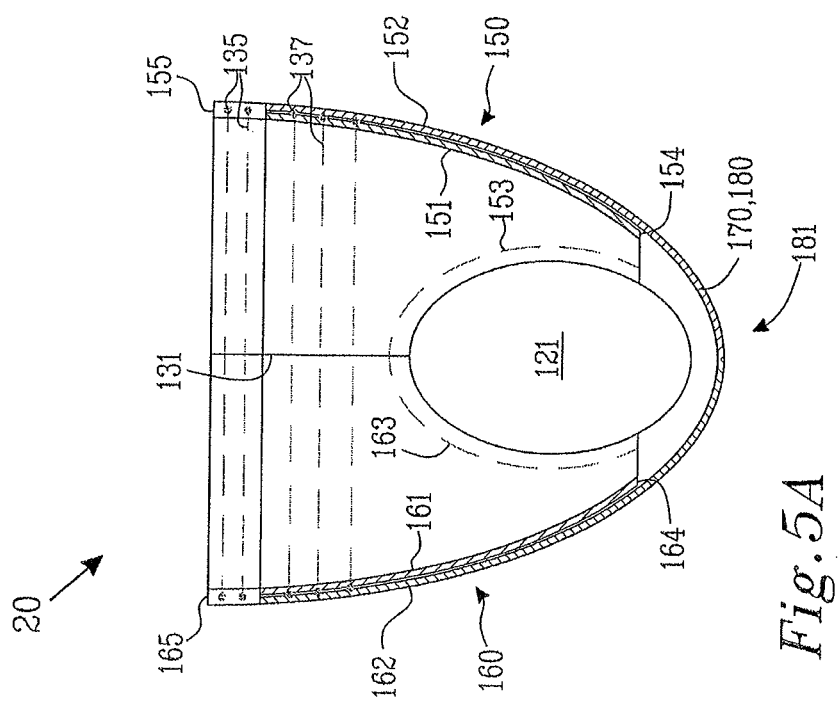
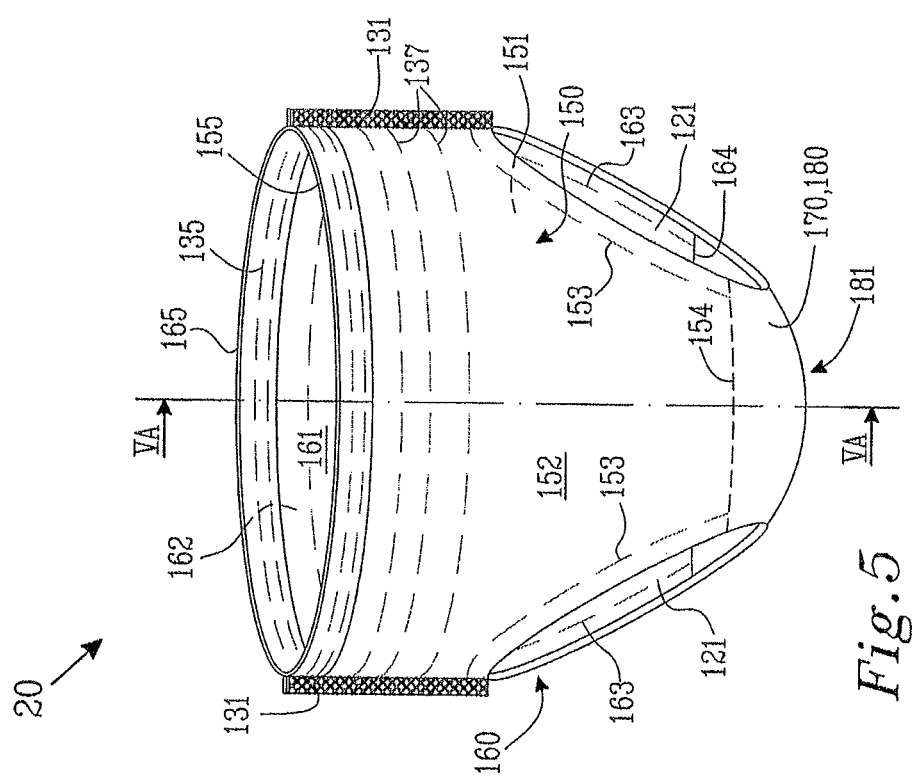

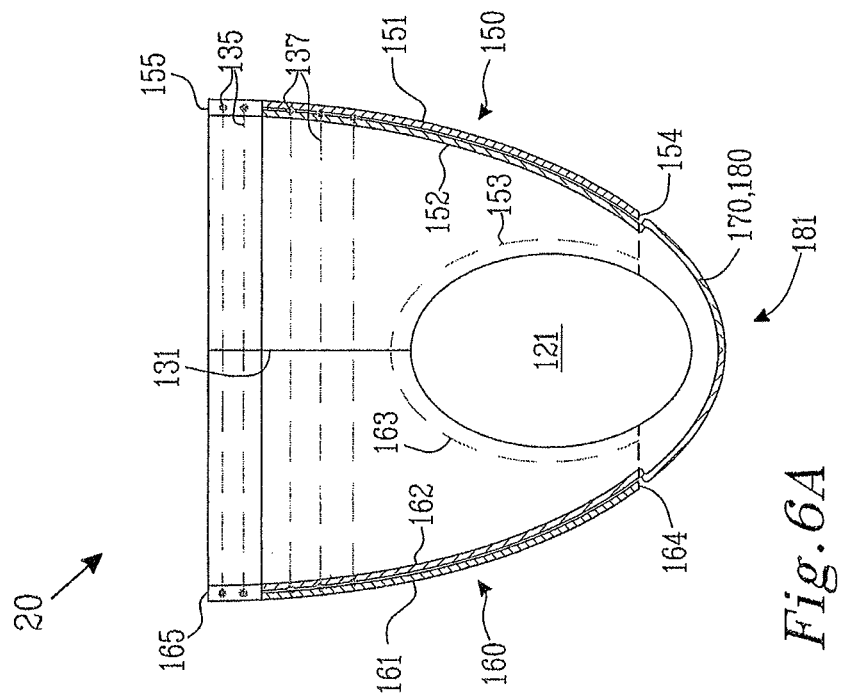
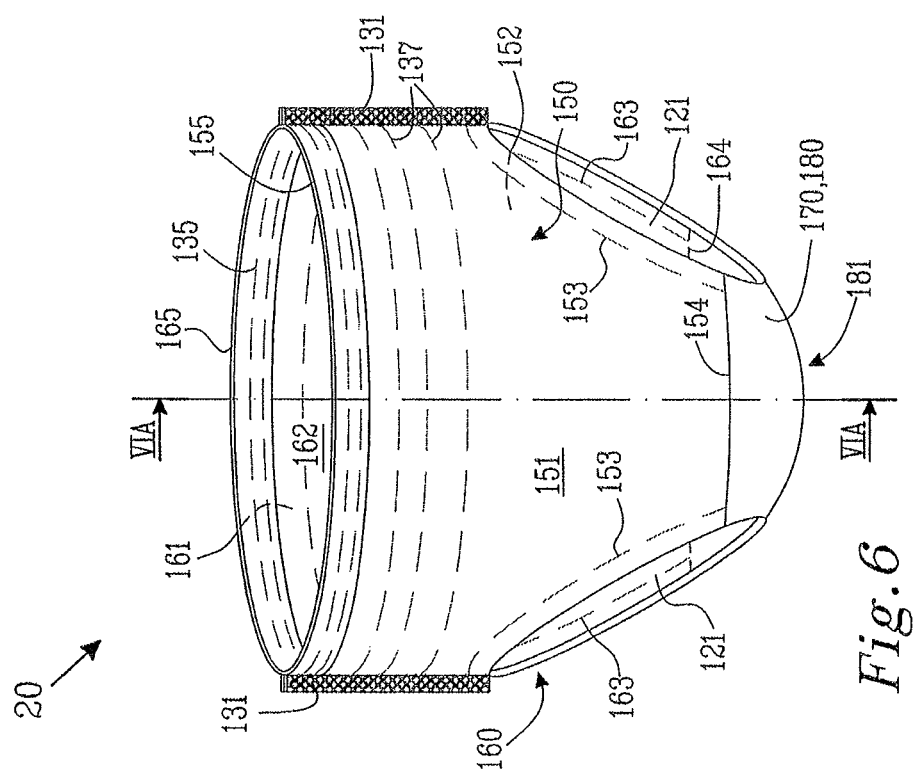

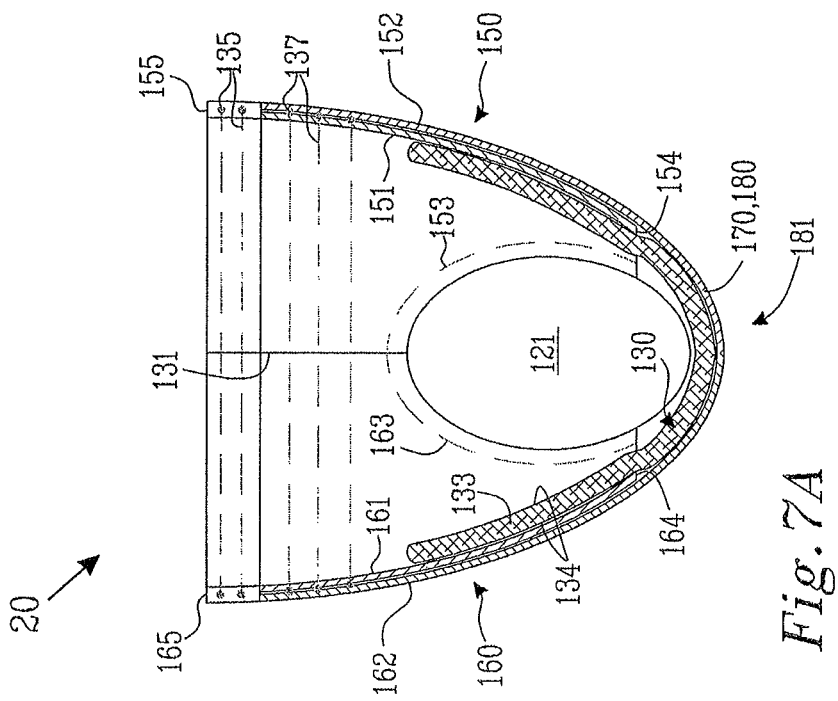
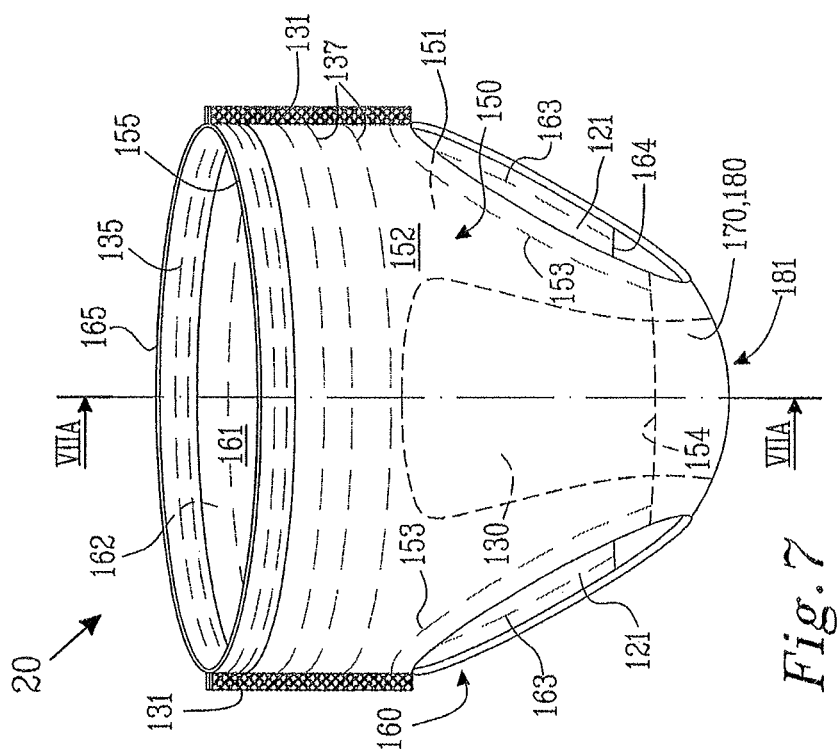

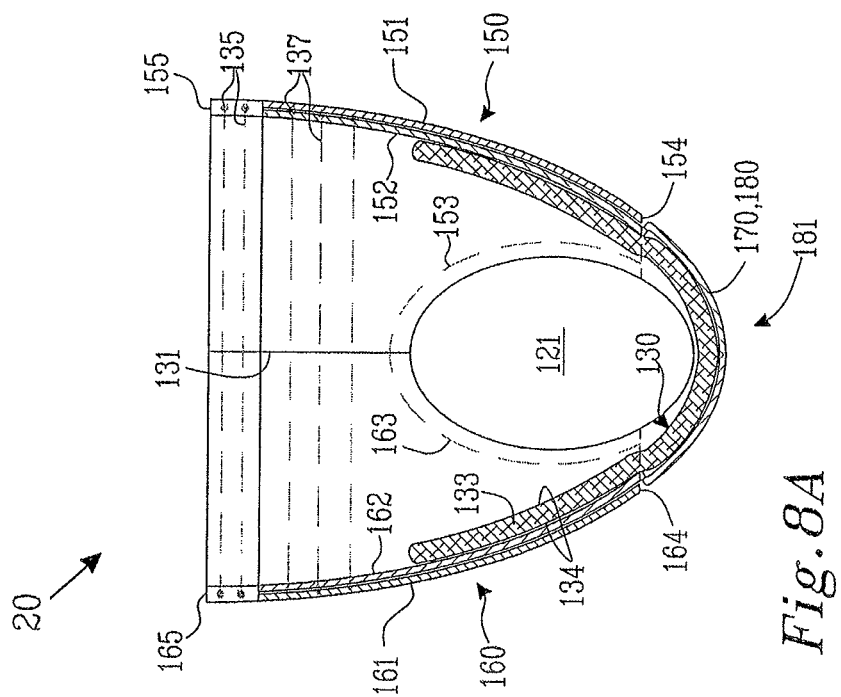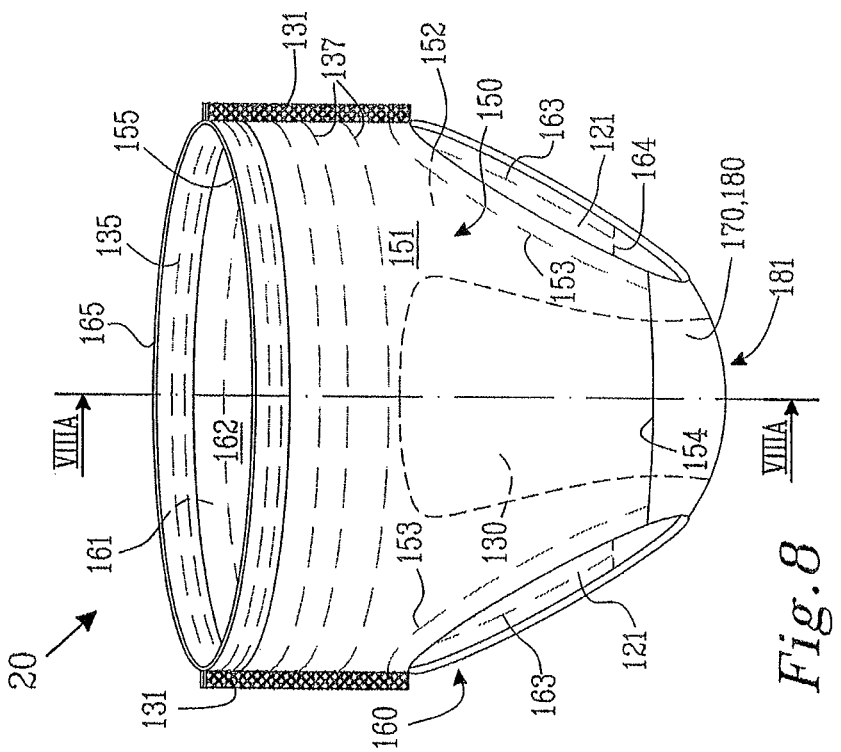

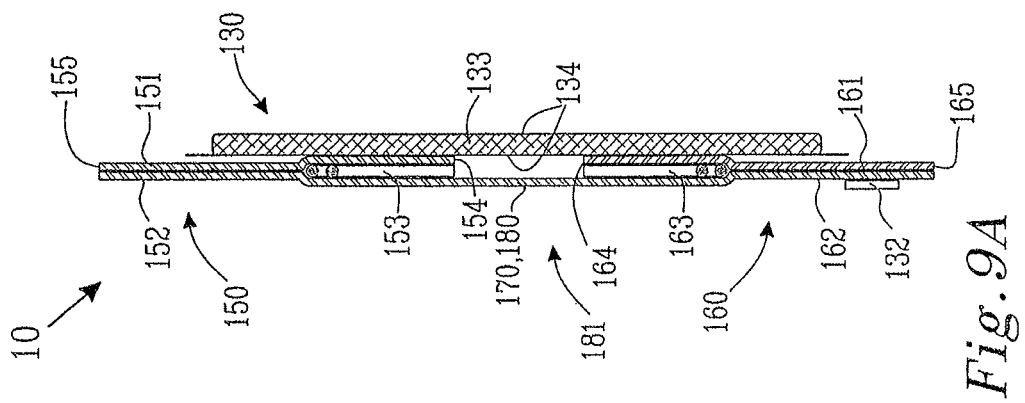
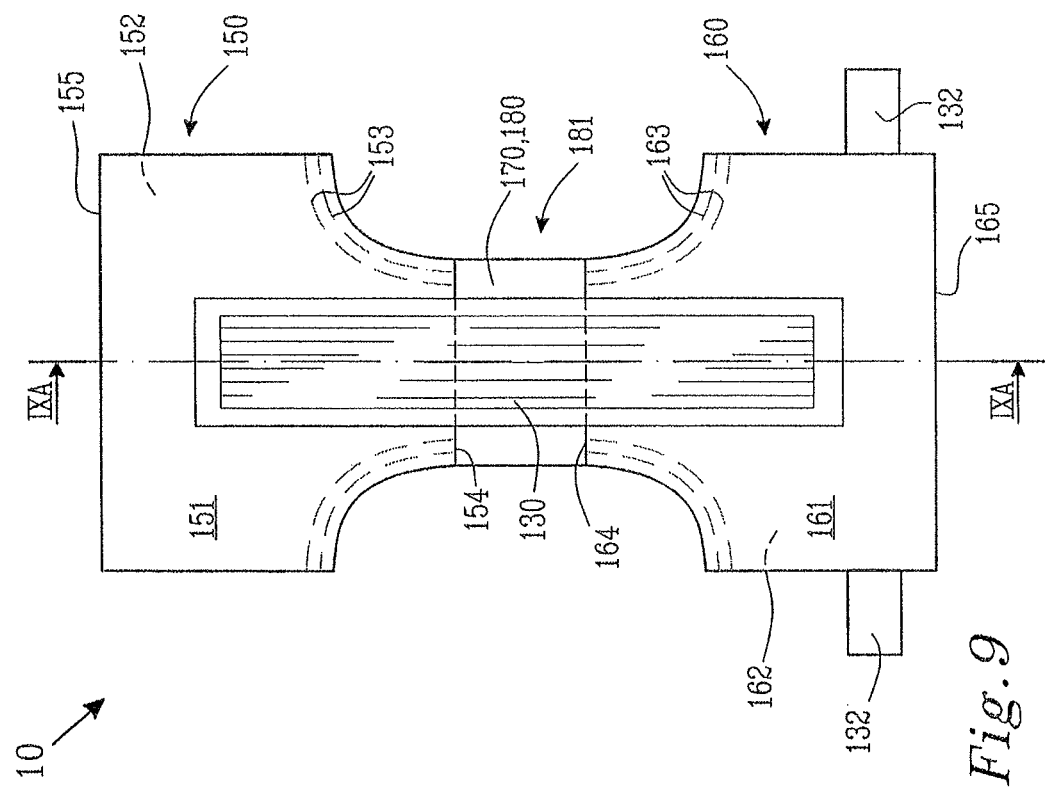

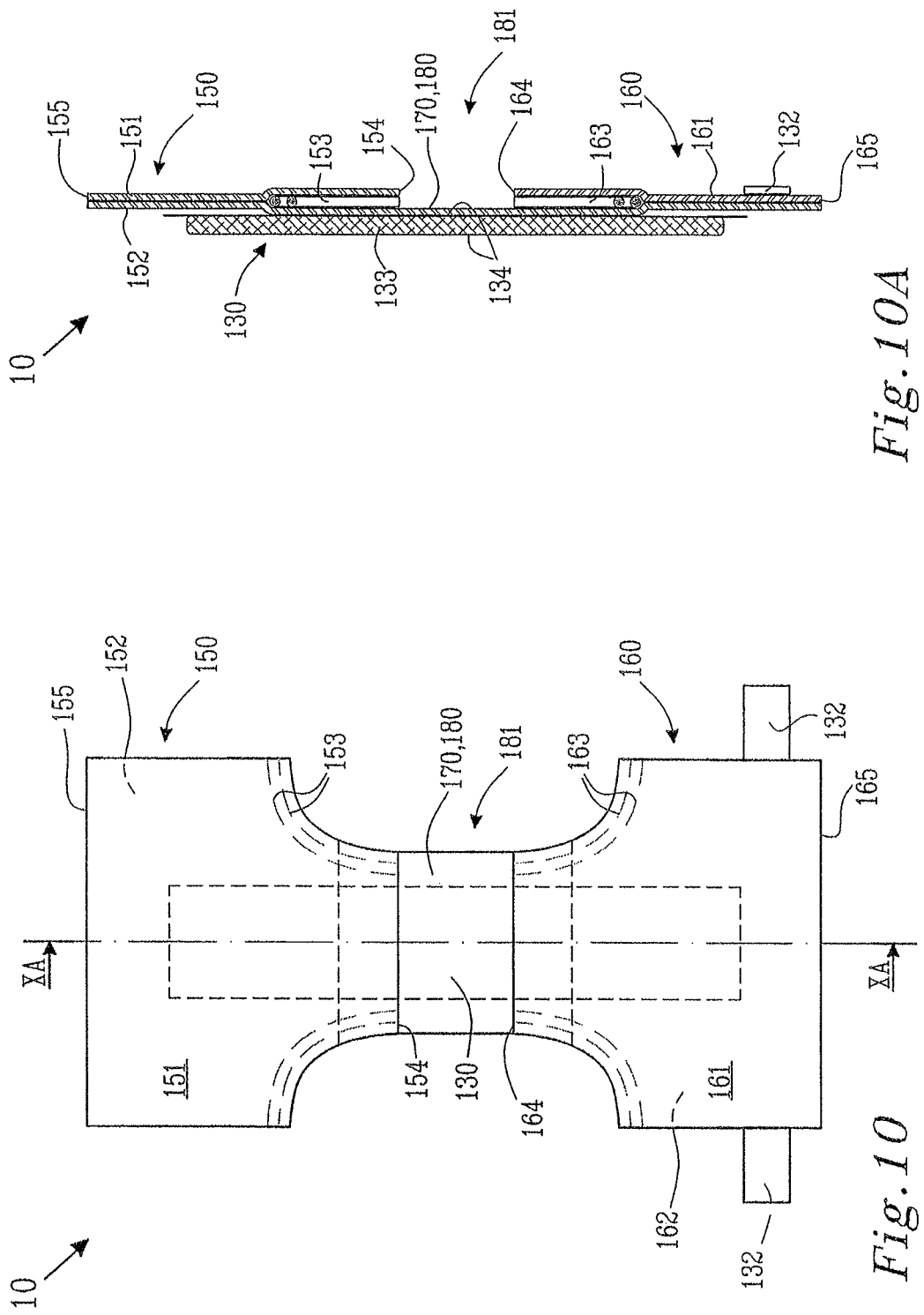

METHOD AND APPARATUS FOR MANUFACTURING ELASTICATED WEBS COMPRISING DISCONTINUOUS ELASTIC THREADS

CROSS-REFERENCE TO PRIOR APPLICATION

This application is a §371 National Stage Application of PCT International Application No. PCT/SE2010/050445 filed Apr. 22, 2010, which claims priority from PCT/SE2009/050468 filed Apr. 30, 2009, both of which are incorporated herein in their entirety.

TECHNICAL FIELD

The present disclosure relates to methods for manufacturing an elasticated web. The disclosure further relates to an apparatus for forming the elasticated web. The disclosure also relates to methods for manufacturing an absorbent article. The disclsoure also provides elasticated webs and absorbent articles which can be manufactured using the methods of the disclosure.

BACKGROUND

Absorbent articles, such as diapers or incontinence guards, are articles which are worn adjacent the body, and used for the containment and absorption of bodily exudates, such as urine, blood, faeces and sweat. Such articles are usually supplied with elastic members (commonly in the form of one or more elastic threads). In the interests of manufacturing efficiency and economy, the elastic members are located in selected regions of the article, such as leg openings, waist openings, standing gathers etc. Elastic members have a number of functions—they inter alia help to maintain the article in place on the wearer, they provide the article with a suitable three-dimensional form and they help to seal portions of the article against the skin of the wearer, thus reducing the risk of leakage.

Absorbent articles are manufactured in high volumes, at high speeds. Methods are therefore required which allow the incorporation of elastic members (e.g. in the form of one or more elastic threads) into or onto other components of an absorbent article during manufacture. Elastic members are usually only located in regions of the absorbent article, but are often supplied in continuous form (e.g. on a roll), so one or more steps of cutting the elastic members is usually required. This in turn leads to difficulties in maintaining the correct tension in the elastic members, and may cause crumpling, foreshortening or wrinkling of the elasticated components.

A particular issue is found with elastic members located in the crotch portion of absorbent articles—i.e. that portion which is located between the wearer's legs when the article is worn. It is generally undesirable that elastic members are located in the crotch portion, as they can cause chafing/rubbing in this sensitive area. In addition, elastic members which are arranged across an absorbent core can cause the core to deform. This in turn causes problems in terms of appearance (due to bunching) and liquid handling (due to undesired compression of the absorbent core causing liquid-channelling creases).

U.S. Pat. Nos. 5,660,657 and 5,643,396 disclose methods for constructing garments including stretched elastic. U.S. Pat. No. 4,379,016 describes a method and device for applying elastic strips in sections onto a web of material. U.S. Pat. No. 6,179,946 describes a process for making a composite sheet. U.S. Pat. Nos. 6,482,278 and 6,521,320 disclose pant-type diapers, and methods for their manufacture. WO 97/00654 discloses an apparatus and a method for applying elastic thread to a web.

SUMMARY

The present disclosure aims to address the shortcomings associated with the prior art. In particular, the present disclosure aims to provide a method for providing an elasticated web having discontinuous elastic threads, in which the tension in the elastic threads can be readily controlled, in which cutting of the elastic threads can be accurately controlled, and in which material wastage is minimized. The process should occur without having to remove or add any non-elastic material. In addition, it is advantageous to be able to control the fate of waste material, particularly at the disposal stage. Desirably, the method can be implemented on known or commercially-available machinery without substantial changes to the machinery. These, and further advantages will be apparent from the following description and claims.

In a first aspect, a method for manufacturing an elasticated web is provided having discontinuous elastic threads. The method includes the steps of:

a. providing a first web, the first web having a primary extension in the machine direction, first and second faces and a first edge and a second edge, the first and second edges extending in the machine direction;

b. providing a second web, the second web also having a primary extension in the machine direction, first and second faces and a first edge and a second edge, the first and second edges extending in the machine direction;

c. providing a third web, the third web having a primary extension in the machine direction, first and second faces and a first edge and a second edge, the first and second edges extending in the machine direction;

d. arranging the third web to lie adjacent and substantially parallel with the first web in a spaced arrangement with the first faces of the webs facing the same direction, such that the first edges of respective first and third webs are adjacent;

e. applying a first adhesive to at least a portion of the first face of the first web or to at least a portion of the first face of the second web;

f. applying a second adhesive to at least a portion of the first face of the third web or to at least a portion of the first face of the second web;

g. applying at least one first elastic thread on at least the portion of the first face of the first web or on at least the portion of the first face of the second web which includes the first adhesive; wherein the at least one first thread is applied in a first pattern, the first pattern oscillating in the cross-direction and extending in the machine direction, h. applying at least one second elastic thread on at least the portion of the first face of the third web or to at least the portion of the first face of the second web which includes the second adhesive; wherein the at least one second elastic thread is applied in a second pattern; the second pattern oscillating in the cross-direction and extending in the machine direction, i. applying a portion of the first face of the second web on the first face of the first web, and fixing the first and second webs together such that the at least one first elastic thread is partly sandwiched between the first faces of respective first and second webs; such that the first pattern extends over the first edge of the first web to form first loops in the first elastic thread which project in the cross-direction from the first edge of the first web;

j. applying a portion of the first face of the second web on the first face of the third web, and fixing the third and second webs together such that the at least one second elastic thread is partly sandwiched between the first faces of respective second and third webs; such that the second pattern extends over the first edge of the third web to form second loops in the second elastic thread which project in the cross-direction from the first edge of the third web; and such that the first and second patterns are synchronized such that the point in the machine direction at which the first elastic threads are located furthest from the first edge of the first web corresponds substantially to the point in the machine direction at which the second elastic threads are located furthest from the first edge of the third web;

k. securing the first loops of the first elastic threads in a first loop retaining means including at least one resilient belt and at least one anvil, the loop retaining means being located adjacent the first edge of the first web;

l. securing the second loops of the second elastic threads in a second loop retaining means including at least one resilient belt and at least one anvil, the second loop retaining means being located adjacent the first edge of the third web;

m. cutting all the first elastic threads substantially at the point at which each first elastic thread crosses the first edge of the first web such that the loops become detached from the first web;

n. cutting all the second elastic threads substantially at the point at which each second elastic thread crosses the first edge of the third web such that the loops become detached from the third web.

Step d. can take place at any point in the process before step i. so as to provide an elasticated web having discontinuous elastic threads.

Steps e.-l. of this method may occur substantially simultaneously in a single nip.

The resilient belt of the first loop retaining means and the resilient belt of the second loop retaining means may be comprised by a single wide resilient belt.

In a particular embodiment, the first loop retaining means includes at least one first and at least one second resilient belt which are located adjacent the first edge of the first web. Similarly, the second loop retaining means may include at least one third and at least one fourth resilient belt which are located adjacent the first edge of the third web. As a further option, a single wide resilient belt may include the third resilient belt and the first resilient belt, and a single wide resilient belt may include the fourth resilient belt and the second resilient belt.

The at least one anvil may be a central cylinder.

In a second aspect, a method for manufacturing pant-type articles from the elasticated web made in the first aspect is provided. This method includes the steps of:

a. carrying out the method of the first aspect, so to provide an elasticated web having discontinuous elastic threads in which at least one first discontinuous elastic thread is sandwiched between the first faces of respective first and second webs; and at least one second discontinuous elastic thread is sandwiched between the first faces of respective third and second webs;

b. cutting out a leg region of the elasticated web defined substantially between discontinuous elastic threads of the first and third webs so as to form leg openings;

c. folding the elasticated web along a fold-line so that first and second edges of the elasticated web become arranged substantially adjacent one another and substantially parallel;

d. joining the folded elasticated web along cutting lines, the cutting lines extending substantially in the cross direction from the first and second edges of the elasticated web to the fold-line, the cutting lines being located substantially at the point at which the discontinuous elastic threads are located furthest from the fold-line; to form side-seams;

e. cutting the elasticated web along the cutting lines such that the elasticated web remain joined on either side of the cut.

Steps b. and c. can take place in any order, so as to thereby provide pant-type articles.

This method may include the additional step of: placing an absorbent packet so as to overlie at least a portion of the first web, second and/or the third web, and fixing the absorbent packet to at least one of the first, second and/or third webs; after step a., but before step c.

In a third aspect, a method for manufacturing absorbent articles from the elasticated web made in the first aspect is provided. The method includes the steps of a. carrying out the method of the first aspect, so to provide an elasticated web having discontinuous elastic threads in which at least one first dicontinuous elastic thread is sandwiched between the first faces of respective first and second webs; and at least one second discontinuous elastic thread is sandwiched between the first faces of respective third and second webs;

b. placing an absorbent packet so as to overlie at least a portion of the first web, second and/or the third web, and fixing the absorbent packet to at least one of the first, second and/or third webs;

c. cutting out a region of the elasticated web defined substantially between discontinuous elastic threads of the first and third webs, so as to form leg openings;

d. providing fastening means on the elasticated web;

e. cutting the elasticated web along cutting lines, cutting lines extending substantially in the cross direction from the first edge to the second edge of the elasticated web, the cutting lines being located substantially at the point at which the discontinuous elastic threads are located furthest from the first edges of the first and third webs; so as to provide absorbent articles.

In a fourth aspect, an apparatus is provided for manufacturing the elasticated web according to the method of the first aspect. The apparatus includes:

a first web supply means for supplying the first web;

a second web supply means for supplying the second web;

a third web supply means for supplying the third web;

a first elastic thread supply means for supplying the at least one first elastic thread;

a second elastic thread supply means for supplying the at least one second elastic thread;

a first adhesive supply means for supplying the first adhesive;

a second adhesive supply means for supplying the second adhesive;

a cutting means for cutting the first and second elastic threads;

The first adhesive supply means is arranged so as to apply a first adhesive to at least a portion of the first face of first web or to at least a portion of the first face of the second web;

The first elastic thread supply means is arranged so as to apply at least one first elastic thread on at least the portion of the first face of the first web or on at least the portion of first face of second web which includes the first adhesive. The at least one first elastic thread is applied in a first pattern, the first pattern oscillating in the cross-direction and extending in the machine direction.

The second adhesive supply means is arranged so as to apply a second adhesive to at least a portion of the first face of the third web or to at least a portion of the first face of the second web.

The second elastic thread supply means is arranged so as to apply at least one second elastic thread on at least the portion of the first face of the third web or on at least the portion of the first face of the second web which includes the second adhesive. The at least one second elastic thread is applied in a second pattern, the second pattern oscillating in the cross-direction and extending in the machine direction.

The second web supply means is arranged so as to apply the first face of the second web on the first face of the first web and the first face of third web, and fix the first and second webs together; and the third and the second webs together; such that the at least one first elastic thread is partly sandwiched between the first faces of respective first and second webs; and the at least one second elastic thread is partly sandwiched between the first faces of respective third and second webs; and such that the first pattern extends over the first edge of the first web to form first loops in the first elastic threads which project in the cross-direction from the first edge of the first web; and such that the second pattern extends over the first edge of the third web to form second loops in the second elastic threads which project in the cross-direction from the first edge of the third web; and such that the first and second patterns are synchronized such that the point in the machine direction at which the first elastic threads are located furthest from the first edge of the first web corresponds substantially to the point in the machine direction at which the second elastic threads are located furthest from the first edge of the third web.

The cutting means arranged so as to cut all the elastic threads substantially at the point at which each first elastic thread crosses the first edge of the first web such that the first loops become detached from the first web; and at the point at which each second elastic thread crosses the first edge of the third web; such that the second loops become detached from the third web.

The apparatus includes first loop retaining means including at least one resilient belt and at least one anvil, the first loop retaining means located adjacent the first edge of the first web and being adapted so as to secure the first loops in the first loop retaining means, and second loop retaining means including at least one resilient belt and at least one anvil, the loop retaining means being located adjacent the first edge of the third web and being adapted so as to secure the second loops in the second loop retaining means.

The first loop retaining means may include at least one first and at least one second resilient belt which are located adjacent the first edge of the first web; and which are adapted so as to secure the first loops of the first elastic thread in a nip between the at least one first and the at least one second resilient belt.

Similarly, the second loop retaining means may include at least one third and at least one fourth resilient belt which are located adjacent the first edge of the third web; and which are adapted so as to secure the second loops of the second elastic thread in a nip between the at least one third and the at least one fourth resilient belt. Optionally, a single wide resilient belt may include the third resilient belt and the first resilient belt, and a single wide resilient belt includes the fourth resilient belt and the second resilient belt.

First, second and third webs may be fixed together in a single nip in the apparatus of the fourth aspect.

In the apparatus of the fourth aspect:
a first web supply means for supplying the first web;
a second web supply means for supplying the second web;
a third web supply means for supplying the third web;
a first elastic thread supply means for supplying the at least one first elastic thread;
a second elastic thread supply means for supplying the at least one second elastic thread;
a first adhesive supply means for supplying the first adhesive;
a second adhesive supply means for supplying the second adhesive;
a cutting means for cutting the first and second elastic threads; and
a first and second loop retaining means
may be arranged peripherally about a single central cylinder.

In a fifth aspect, an apparatus is also provided for manufacturing pant-type articles from the elasticated web manufactured according to the method of the first aspect. This apparatus additionally includes:
a elasticated web supply means for supply of the elasticated web;
optionally, an absorbent packet supply means for supply of absorbent packets;
a leg region cutting means for cutting out leg regions;
a folding means for folding the elasticated web;
a joining means for joining the elasticated web; and
an elasticated web cutting means for cutting elasticated web.

The elasticated web supply means is arranged so as to provide an elasticated web having discontinuous elastic threads in which at least one first discontinuous elastic thread is sandwiched between the first faces of respective first and second webs; and at least one second discontinuous elastic thread is sandwiched between the first faces of respective third and second webs.

The absorbent packet supply means being arranged so as to place an absorbent packet so as to overlie at least a portion of the first web, second web and/or the third web, and to fix the absorbent packet to at least one of the first, second and third webs.

The leg region cutting means being arranged so as to cut out a region of the elasticated web defined substantially between discontinuous elastic threads of the first and third webs, so as to form leg openings.

The folding means arranged so as to fold the elasticated web along a fold-line, so that first and second edges of the elasticated web become arranged substantially adjacent one another and substantially parallel.

The joining means arranged so as to join the folded elasticated web along cutting lines, the cutting lines extending substantially in the cross direction from the first and second edges of the elasticated web to the fold-line, the cutting lines being located substantially at the point at which the discontinuous elastic threads are located furthest from the fold-line; to form side-seams.

The elasticated web cutting means being arranged so as to cut the elasticated web along the cutting lines such that the elasticated web remains joined on either side of the cut.

In a sixth aspect, an apparatus is provided for manufacturing absorbent articles in the form of open diapers from the elasticated web manufactured according to the method of the first aspect. This apparatus additionally includes:

an elasticated web supply means for supply of the elasticated web;
an absorbent packet supply means for supply of absorbent packets;
a leg region cutting means for cutting out leg regions;
a elasticated web cutting means for cutting elasticated web; and
a fastening supply means for supply of fastening means.

The elasticated web supply means is arranged so as to provide an elasticated web having discontinuous elastic threads in which at least one first discontinuous elastic thread is sandwiched between the first faces of respective first and second webs; and at least one second discontinuous elastic thread is sandwiched between the first faces of respective third and second webs.

The absorbent packet supply means being arranged so as to place an absorbent packet so as to overlie at least a portion of the first web, second web and/or the third web, and to fix the absorbent packet to at least one of the first, second and third webs.

The leg region cutting means being arranged so as to cut out a region of the elasticated web defined substantially between discontinuous elastic threads of the first and third webs, so as to form leg openings.

The fastening supply means arranged so as to provide fastening means on the elasticated web.

The elasticated web cutting means being arranged so as to cut the elasticated web along cutting lines, the cutting lines extending substantially in the cross direction from the first edge to the second edge of the elasticated web, the cutting lines being located substantially at the point at which the discontinuous elastic threads are located furthest from the first edges of the first and third webs.

The at least one anvil may be a central cylinder.

Definitions

The "machine-direction" should be understood to mean the principal direction of travel of the components in an automated process. The "cross-direction" should be understood to mean the direction perpendicular to the machine direction, in the plane of the components.

The term "absorbent article" refers to products that are placed against the skin of the wearer to absorb and contain body exudates, like urine, faeces and menstrual fluid.

The disclosure mainly refers to disposable absorbent articles, which means articles that are not intended to be laundered or otherwise restored or reused as an absorbent article after use. The term includes diapers (both open diapers and pant diapers) and incontinence guards.

BRIEF DESCRIPTION OF THE DRAWINGS

The embodiments of the invention will now be more closely described with reference to the enclosed schematic figures, in which:

FIG. 1A is an expanded cross-sectional view along the line IA-IA in FIG. 1;

FIG. 1B is an expanded cross-sectional view along the line IB-IB in FIG. 1;

FIG. 4 shows how an open diaper may be produced from the elasticated web made by the method of FIG. 1;

FIG. 5 shows an embodiment of a pant-type article which can be made using a method in accordance with an embodiment of the invention;

FIG. 5A is a cross-sectional view along line VA-VA of FIG. 5;

FIG. 6 shows an embodiment of a pant-type article which can be made using a method in accordance with an embodiment of the invention;

FIG. 6A is a cross-sectional view along line VIA-VIA of FIG. 6;

FIG. 7 shows an embodiment of a pant-type article which can be made using a method in accordance with an embodiment of the invention;

FIG. 7A is a cross-sectional view along line VIIA-VIIA of FIG. 7;

FIG. 8 shows an embodiment of a pant-type article which can be made using a method in accordance with an embodiment of the invention;

FIG. 8A is a cross-sectional view along line VIIIA-VIIIA of FIG. 8;

FIG. 9 shows an embodiment of an open diaper which can be made using a method in accordance with an embodiment of the invention;

FIG. 9A is a cross-sectional view along line IXA-IXA of FIG. 9;

FIG. 10 shows an embodiment of an open diaper which can be made using a method in accordance with an embodiment of the invention;

FIG. 10A is a cross-sectional view along line XA-XA of FIG. 10;

DETAILED DESCRIPTION OF PREFERRED EMBODIMENTS

Figure 1:
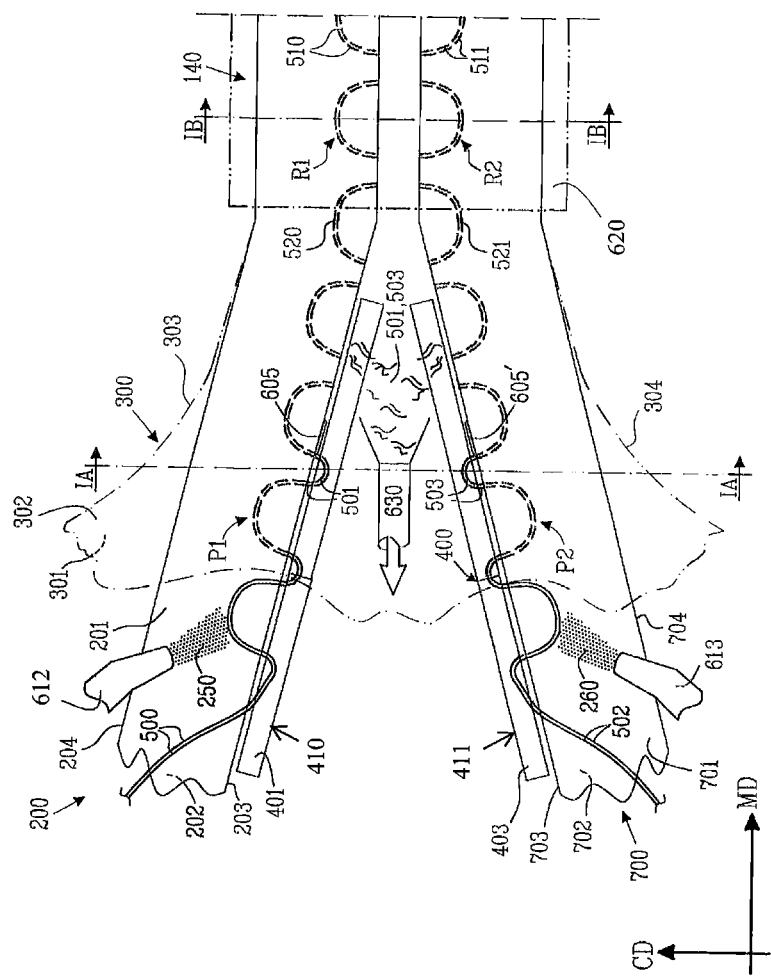
FIG. 1 is a simplified view of a method for manufacturing an elasticated web.

The illustration in FIG. 1 provides a method for manufacturing an elasticated web 140 having discontinuous elastic threads 510, 511. The elasticated web 140 includes a laminate of first 200 and second 300 webs, with discontinuous elastic threads 510 sandwiched between the first 200 and second 300 webs. On a different portion of the second web 300, a third web 700 is laminated, with discontinuous elastic threads 511 sandwiched between the third 700 and second 300 webs.

A first web 200 is provided, the first web 200 having a primary extension in the machine direction (MD), first 201 and second 202 faces and a first edge 203 and a second edge 204, said first and second edges 203, 204 extending in the machine direction (MD). First 203 and second 204 edges of the first web 200 are typically straight and parallel to one another. The first web 200 is transported essentially continuously in the machine direction from e.g. a roll. Typically, the first web 200 has an extension in the cross direction (CD) of between 10 and 25 cm for a baby diaper and 20-50 cm for an adult incontinence pant, particularly between 13-20 cm for a baby diaper and 30-43 cm for an adult incontinence pant.

The first web 200 may include a nonwoven material (e.g. spunbond, meltblown, carded, hydroentangled, wetlaid etc).

The fibres of the nonwoven material may be natural (e.g. rayon or cellulose fibres) or artificial (e.g. polymeric fibres such as polyolefin fibres, e.g. polyethylene or polypropylene fibres). The first web 200 may alternatively include a plastic film, e.g. a polyolefin film such as polyethylene or polypropylene. The first web 200 may even include a laminate of two or more nonwoven layers, or a laminate of one or more nonwoven layers with one or more plastic films. Suitably, the first web 200 has a basis weight of between 10-40 g/m$^2$. The first web 200 should suitably be air-permeable.

A second web 300 is also provided, the second web 300 also having a primary extension in the machine direction (MD), first 301 and second 302 faces and a first edge 303 and a second edge 304, the first and second edges 303, 304 extending in the machine direction (MD).

The second web 300 may include one or more nonwoven materials, plastic films, or laminates of two such materials, in the same way as described for the first web 200, above. First 303 and second 304 edges of the second web 300 are typically straight and parallel to one another. The second web 300 may have the same dimensions as the first web 200, as shown in FIG. 1. However, it may be possible that the second web 300 has an extension in the cross-direction (CD) which is greater than or less than that of the first web 200. Suitably, the second web 300 has a basis weight of between 10-40 g/m$^2$. The second web 300 should be air-permeable.

A third web 700 is also provided, the third web 700 having a primary extension in the machine direction (MD), first 701 and second 702 faces and a first edge 703 and a second edge 704, the first and second edges 703, 704 extending in the machine direction (MD). The second web 300 typically (but not necessarily) has an extension in the cross-direction (CD) which is equal to or greater than the combined extension of the first 200 and third 700 webs in the cross-direction (CD). FIG. 1 shows that the second web 300 has an extension in the cross-direction (CD) which is substantially equal to the combined extension of the first 200 and third 700 webs in the cross-direction (CD), plus the spacing between the first 200 and third webs 700 (i.e. the "crotch gap").

The material of the third 700 web may be selected from any material given for the first web 200, above. Similarly, the material of the second web 300 may be selected from any material given for the first web 200, above. It may even be possible that the first 200 and third 700 webs originate from the same web which has been split into first 200 and third 700 webs.

The third web 700 is arranged to lie adjacent and substantially parallel with the first web 200, in a spaced arrangement with the first faces 201, 701 of the webs 200, 700 facing the same direction, such that the first edges 203, 703 of respective first 200 and third 700 webs are adjacent. This can be achieved by arranging first 200 and third webs 700 in parallel prior to applying adhesive and/or elastic threads. In effect, first 200 and third 700 webs may be processed in parallel through the same apparatus. First 200 and third 700 webs may even originate from the same single web (not shown), which is split in the machine direction to provide parallel first and third webs 200, 700. Alternatively, first 200 and third 700 webs may be processed separately up to this point, and aligned in the appropriate manner just prior to the second web 300 being applied in the following steps.

In that first 200 and third 700 webs are arranged to lie adjacent and substantially parallel, they do not overlap when fixed to the second web 300. In effect, the second web 300 bridges the space between the first 200 and third 700 webs in the cross-direction (CD), thereby creating the elasticated web 140.

A first adhesive 250 is applied to at least a portion of the first face 201 of the first web 200. Alternatively, the first adhesive 250 is applied to at least a portion of the first face 301 of the second web 300.

The first adhesive 250 may be sprayed on the first 200 or second 300 web, as shown in FIG. 1, but other methods of application may also be used, e.g. slot-coating, multi-bead coating, extrusion or rolling. A particular method of applying adhesive is slot-coating. The first adhesive 250 is typically applied to the first web 200 in amounts between 5 and 30 gsm, particularly between 5 and 15 gsm.

Suitable adhesives for the first adhesive 250 may be e.g. H4281RF from Bostik, NW1002 from HB Fuller GmbH or Dispomelt 5482 from National S&C.

The first adhesive 250 may be applied to the entire first face 201 of the first web 200. However, in the interests of economy, the first adhesive 250 is only applied to a portion of the first face 201 of the first web 200. The first adhesive 250 may be applied to the first web 200 in a substantially uniform manner, but particularly, the first adhesive 250 is applied to the first web 200 in a first pattern which corresponds to the first pattern (P1) in which the first elastic threads 500 are applied to the first web 200 (see below).

Likewise, a second adhesive 260 is applied to at least a portion of the first face 701 of the third web 700. Alternatively, the second adhesive 260 is applied to at least a portion of the first face 301 of the second web 300. Should first and second adhesives 250, 260 both be applied to the second web 300, they should suitably be applied in different areas thereof, in a non-overlapping manner. The first and second adhesive 250, 260 are particularly applied to the second web 300 adjacent to one another in the cross-direction CD. Second 260 adhesive may be selected from any of the adhesives given for the first adhesive 250, above, and may include the same adhesive. Application methods for the second adhesive 260 may also be selected from any means described above.

At least one first elastic thread 500 is applied on at least the portion of the first face 201 of the first web 200 or on at least the portion of the first face 301 of the second web 300 which includes the first adhesive 250. The first elastic threads 500 will eventually form the leg elastics of a pant-type article 20, or an absorbent article 10 of the open-diaper type. Suitable first elastic threads 500 include e.g. C17A from Plymouth SA (synthetic elastic, profile 0.2 mm×2 mm×6 ends to be split up in the process) or XA T-262P 1A216 from Invista (1100 dtex single thread on spool, circular profile). Although the term "thread" is used in the present specification, the term is to be interpreted as including narrow bands of elastic material (e.g. with a width of less than 1 cm). The first elastic threads 500 are supplied in a continuous manner from e.g. a roll. It may be possible that only one first elastic thread 500 is applied to the first web 200, although more than one, e.g. 2, 3 or even 4 elastic threads 500 may be applied. In the case a plurality of first elastic threads 500 is used, all elastic threads 500 should be applied substantially in parallel. The at least one first thread 500 is applied in a first pattern (P1), the first pattern (P1) oscillating in the cross-direction (CD) and extending in the machine direction (MD), as shown in FIG. 1.

In the same way as for the first web 200, at least one second elastic thread 502 is applied on at least the portion of said first face 701 of said third web 700 or on at least the portion of said first face 301 of said second web 300 which comprises said second adhesive 260. The at least one second elastic thread 502 is applied in a second pattern (P2), said second pattern (P2) oscillating in the cross-direction (CD) and extending in the machine direction (MD). The materials which may be used for the second elastic threads 502 are the same as those of the first elastic threads 500.

A portion of the first face 301 of the second web 300 is applied on the first face 201 of the first web 200, and the first 200 and second webs 300 are fixed together such that the at least one first elastic thread 500 is partly sandwiched between the first faces 201, 301 of respective first and second webs 200, 300, such that the first pattern (P1) extends over the first edge 203 of the first web 200 to form first loops 501 in the first elastic thread 500 which project in the cross-direction (CD) from the first edge 203 of the first web 200, see FIG. 1. FIG. 1 shows a wavy pattern (P1); however, the first pattern (P1) can take a variety of oscillating forms, and may include one or more straight (linear) sections, a zig-zag form, a sinusoidal form or variations on such patterns.

First and second webs 200, 300 may be fixed together by any suitable means, e.g. thermal welding, ultrasonic welding or adhesion. Adhesion is most preferred. Suitably, the first adhesive 250 which is used to secure the at least one first elastic thread 500 to the first web 200 can also be used to secure the first 200 and second 300 webs together. Additional adhesive as required may be applied to the first face 301 of the second web 300 and/or the first face 201 of the first web 200. First 200 and second 300 webs are suitably fixed to one another across substantially their entire area of overlap.

Similarly a portion of the first face 301 of the second web 300 is applied on the first face 701 of the third web 700, and the third 700 and second webs 300 are fixed together such that the at least one second elastic thread 502 is partly sandwiched between the first faces 301, 701 of respective second and third webs 300, 700 such that the second pattern (P2) extends over the first edge 703 of the third web 700 to form second loops 503 in the second elastic thread 502 which project in the cross-direction (CD) from the first edge 703 of the third web 700, see FIG. 1. FIG. 1 shows an essentially wavy pattern (P2); however, the second pattern (P2) can take a variety of oscillating forms, and may include one or more straight (linear) sections, a zig-zag form, a sinusoidal form or variations on such patterns. The second pattern (P2) may take the same form as the first pattern (P1); however, it is preferred that the second pattern (P2) is different to the first pattern (P1). Second 300 and third 700 webs may be fixed together by any suitable means, such as those discussed above for the first 200 and second 300 webs. Suitably, the second adhesive 260 which is used to secure the at least one second elastic thread 502 to the second web 300 can also be used to secure the second 300 and third 700 webs together.

The first and second patterns (P1, P2) which the elastic threads 500, 502 make on the first 200 and third 700 webs are synchronised as shown in FIG. 1. Synchronisation occurs such that the point in the machine direction (MD) at which the first elastic threads 500 are located furthest from the first edge 203 of the first web 200 corresponds substantially to the point in the machine direction (MD) at which the second elastic threads 502 are located furthest from the first edge 703 of the third web 700. In other words, the first and second patterns P1, P2 have the same repeat frequency and meet and diverge repeatedly in the machine direction.

The first loops 501 of the first elastic threads 500 are secured in first loop retaining means 410 located adjacent the first edge 203 of the first web 200. Suitably, the first loop retaining means 410 is spaced from the first edge 203, so as to allow the subsequent cutting step(s) to take place.

First loop retaining means 410 acts to secure the first loops 501. It is important that first loops 501 are secured, so that—when the leading edge of each first loop 501 is cut in the following steps—the first loop 501 does not simply retract completely, but instead, tension is maintained between the following edge of each loop and the first loop retaining means 410.

First loop retaining means 410 includes at least one resilient belt 401 and at least one anvil 620. As shown in FIG. 1, the first loops 501 of the first elastic threads 500 are secured between said resilient belt 401 and the anvil 620.

In a similar way to the first loops 501, the second loops 503 are secured in second loop retaining means 411 located adjacent the first edge 703 of said third web 700. Suitably, the second loop retaining means 411 is spaced from the first edge 703, so as to allow the subsequent cutting step(s) to take place. As shown in FIG. 1, second loop retaining means 411 includes at least one resilient belt 403 and at least one anvil 620. The second loops 503 of the second elastic threads 502 are therefore secured between the resilient belt 403 and the anvil 620.

The anvil 620 is typically a component made of a hard, non-elastic material such as metal, against which the resilient belts can run. The anvil 620 typically takes the form of a central cylinder 620, about which the components of the apparatus are arranged (see FIG. 2), although other forms are possible (e.g. a plurality of cylinders).

The first loop retaining means 410 may include at least one first 401 and at least one second 402 resilient belt (i.e. two resilient belts) which are located adjacent the first edge 203 of the first web 200. The first loops 501 are therefore secured in a nip 400 between at least one first 401 and at least one second 402 resilient belts. In this case, one of the resilient belts 401, 402 is arranged to run against the anvil 620.

The resilient belts 401, 402, 403, 404 may be made of rubber, or any other suitable resilient material. One resilient belt 401 may have a cross-section such that it can engage with one or more recesses in the other resilient belt 402, or one or more recesses in the anvil 620. To this effect, one resilient belt 401 may include one or more protrusions which can engage with one or more recesses in the other resilient belt 402 or the anvil 620. Alternatively, one resilient belt 401 may have a cross-section which is e.g. circular, semi-circular, oval, triangular or square and which can engage with one or more recesses in the other resilient belt 402 or in the anvil 620. This profiled arrangement allows close contact between the belts 401, 402, and/or the resilient belt and the anvil 620 and allows the loops 501, 503 of the elastic threads 500, 502 to be tightly secured. Alternatively, or additionally, to having recesses/protrusions, the belts 401, 402 may include high-friction surfaces which grip the loops 501, 503 securely.

In that the elasticated web 140 is manufactured in the symmetrical fashion illustrated in FIG. 1, various resilient belts may be comprised by a single wide resilient belt. In particular, the resilient belt 401 of the first loop retaining means 410 and the resilient belt 403 of the second loop retaining means 411 may be comprised by a single wide resilient belt.

As a development of what is shown in FIG. 1, the second loop retaining means 411 may include at least one third 403 and at least one fourth 404 resilient belt (i.e. two resilient belts) which are located adjacent the first edge 703 of the third web 700. The nature and features of the third 403 and fourth 404 resilient belts correspond to those given above for the first loop retaining means 410. In this case, one of the resilient belts 403, 404 is arranged to run against the anvil 620.

It is even possible that a single wide resilient belt includes the third resilient belt 403 and the first resilient belt 401, while a single wide resilient belt includes the fourth resilient belt 404 and the second resilient belt 402. In other words, a pair of wide resilient belts are used instead of four separate resilient belts 401, 402, 403, 404, to capture all loops 501, 503. In this case, it is suitable that the wide resilient belts include profiled arrangements at their cross-directional edges.

Figure 2:
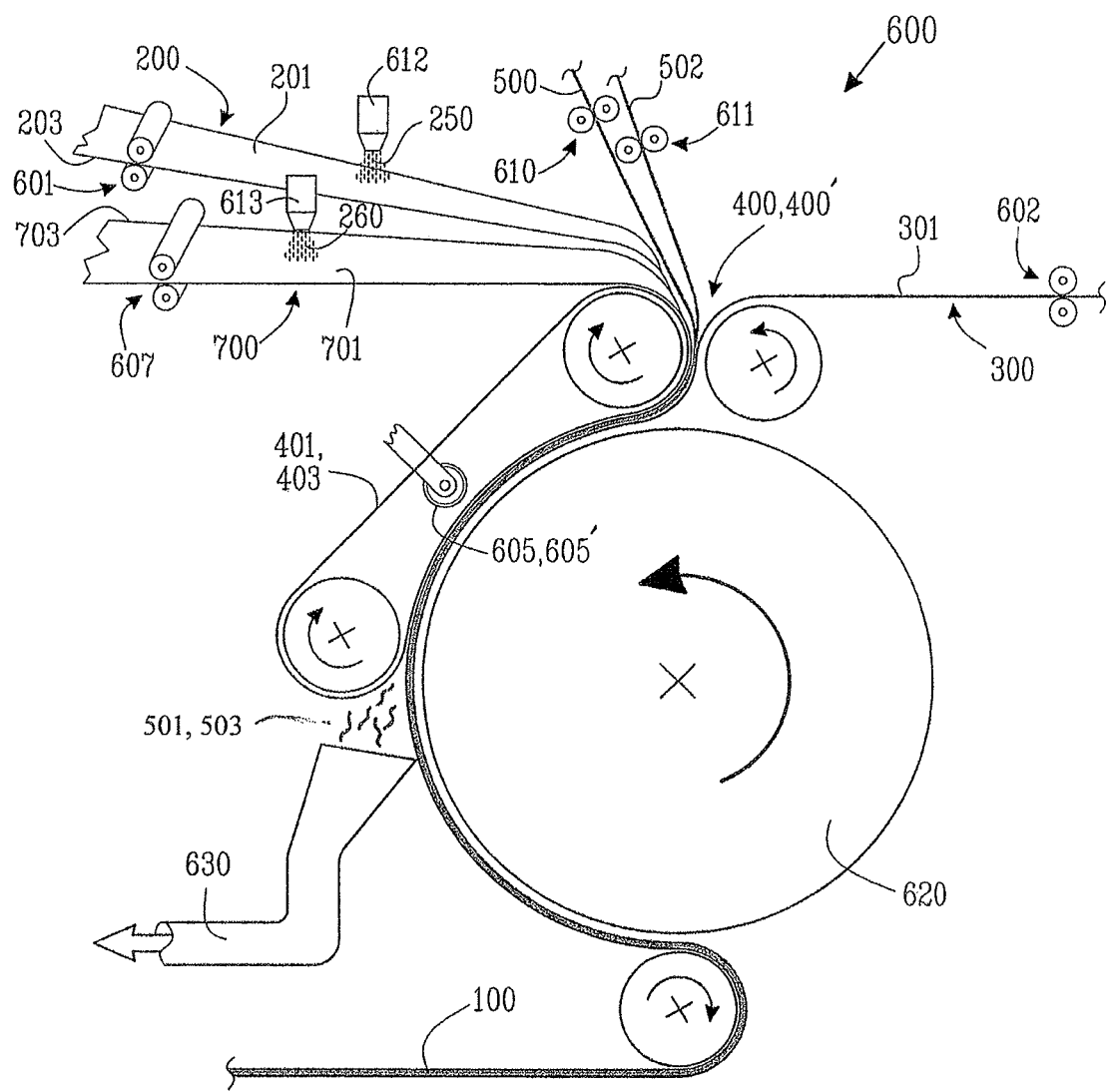
FIG. 2 is a cross-sectional view of an apparatus suitable for providing an elasticated web in accordance with an embodiment of the invention.

While the first elastic threads 500 are still held in the first loop retaining means 410, all the first elastic threads 500 are cut substantially at the point at which each first elastic thread 500 crosses the first edge 203 of the first web 200 such that the first loops 501 become detached from the first web 200. Similarly, all the second elastic threads 502 are cut substantially at the point at which each second elastic thread 502 crosses the first edge 703 of the third web 700 while the second elastic threads 502 are still held in the second loop retaining means 411, such that the second loops 503 become detached from the third web 700. The loops 501, 503 therefore become detached from the first web 200. As shown in FIGS. 1 and 2, the loop retaining means 410, 411 are released, and loops 501, 503 removed from the remainder of the elasticated web 140. Suitably, vacuum means 630 is used to remove the loops 501, 503 from the process.

Cutting of first 500 or second 502 elastic threads should be intermittent, so as not to completely remove the second web 300 from the nascent elasticated web 140. In this case, cuts are only made substantially at each point at which the elastic threads 500, 502 cross the first edge 203 of the first web 200 and the first edge 703 of the third web 700. It is also possible just to cut the elastic threads 500, 502.

An elasticated web 140 having discontinuous elastic threads 510, 511 is thus provided. This elasticated web 140 may be rolled up and stored, or used directly to produce pant-type articles 20 or absorbent articles 10 of the open-diaper type. In that loop retaining means 410, 411 (each in the form of at least one resilient belt 401, 403) is used to retain the elastic threads 500, 502 in the production of the elasticated web 140, undesired pieces of elastic are captured, controlled and safely disposed of during the process. In addition, the tension in the discontinuous elastic threads 510, 511 can be controlled, and cutting of the elastic threads 500, 502 can be performed accurately, as the elastic threads 500, 502 are held in tension by the first and second loop retaining means 410, 411. In addition, in that the loop retaining means 410, 411 are in the form of at least one resilient belt, the loop retaining means can easily pass through one or more nips between rolls (e.g. central cylinder 620), and the tensions in the loop retaining means 410, 411 can be readily adjusted so that they match those present in the first, second and third webs.

The steps of:
- applying a first adhesive 250 to at least a portion of the first face 201 of the first web 200 or to at least a portion of the first face 301 of the second web 300;
- applying a second adhesive 260 to at least a portion of the first face 701 of the third web 700 or to at least a portion of the first face 301 of the second web 300;
- applying at least one first elastic thread 500 on at least the portion of the first face 201 of the first web 200 or on at least the portion of the first face 301 of the second web 300 which includes the first adhesive 250;
- applying at least one second elastic thread 502 on at least the portion of the first face 701 of the third web 700 or to at least the portion of the first face 301 of the second web 300 which includes the second adhesive 260;
- applying a portion of the first face 301 of the second web 300 on the first face 201 of the first web 200, and fixing the first 200 and second webs 300 together such that the at least one first elastic thread 500 is partly sandwiched between the first faces 201, 301 of respective first and second webs 200, 300; such that the first pattern P1 extends over the first edge 203 of the first web 200 to form first loops 501 in the first elastic thread 500 which project in the cross-direction CD from the first edge 203 of the first web 200;
- applying a portion of the first face 301 of the second web 300 on the first face 701 of the third web 700, and fixing the third 700 and second webs 300 together such that the at least one second elastic thread 502 is partly sandwiched between the first faces 301, 701 of respective second and third webs 300, 700; such that the second pattern (P2) extends over the first edge 703 of the third web 700 to form second loops 503 in the second elastic thread 502 which project in the cross-direction (CD) from the first edge 703 of the third web 700; and such that the first and second patterns (P1, P2) are synchronised such that the point in the machine direction (MD) at which the first elastic threads (500) are located furthest from the first edge 203 of the first web (200) corresponds substantially to the point in the machine direction (MD) at which the second elastic threads 502 are located furthest from the first edge 703 of the third web 700;
- securing the first loops 501 of the first elastic threads 500 in a first loop retaining means 410 including at least one resilient belt 401 and at least one anvil 620, and being located adjacent the first edge 203 of the first web 200;
- securing the second loops 503 of the second elastic threads 502 in a second loop retaining means 411 including at least one resilient belt 403 and at least one anvil 620, and being located adjacent the first edge 703 of the third web 700; may occur substantially simultaneously in a single nip 400.

FIG. 1A is an expanded cross-sectional view of the nascent elasticated web 140 along the line IA-IA in FIG. 1, i.e. prior to cutting the continuous elastic threads 500, 502. It shows the first web 200, the second web 300 and the third web 700. Elastic threads 500 (which project in the cross-direction (CD) from the first edge 203 of the first web 200) are secured between first resilient belt 401 and the central cylinder 620. Elastic threads 502 (which project in the cross-direction (CD) from the first edge 703 of the third web 700) are secured between third resilient belt 403 and the central cylinder 620. In that the second web 300 extends between the first web 200 and the third web 700, it too is secured between the resilient belts 401, 403 and the central cylinder 620. In addition, FIG. 1A shows the resilient belts 401 403 having a particular profile which promotes a secure grip on the elastic threads. For example, the resilient belts 401, 403 shown in FIG. 1A has a pointed profile.

FIG. 1B is an expanded cross-sectional view of the elasticated web 140 along the line IB-IB in FIG. 1; i.e. after cutting the elastic threads 500, 502. It shows the first web 200, the second web 300 and the discontinuous elastic threads 510 laminated between first 200 and second 300 webs. In a similar way, discontinuous elastic threads 511 are laminated between third 700 and second 300 webs. FIG. 1B shows pairs of elastic threads 510, 511; however, it is also conceivable that a lesser or greater number of elastic threads 510, 511 are included. In particular, it is useful to have more elastic threads in the portion of the elasticated web 140 which is to become the rear portion of a pant-type article 20, or an absorbent article 10.

The method provides an elasticated web 140. The elasticated web 140 is illustrated in FIG. 1, and in cross-section in FIG. 1B. The elasticated web 140 has discontinuous elastic threads 510, 511, and includes:
- a first web 200, the first web 200 having a primary extension in the machine direction (MD), first 201 and second 202 faces and a first edge 203 and a second edge 204, the first and second edges 203, 204 extending in the machine direction (MD);

a second web 300, the second web 300 having a primary extension in the machine direction (MD), first 301 and second 302 faces and a first edge 303 and a second edge 304, the first and second edges 303, 304 extending in the machine direction (MD); and third web 700, the third web 700 having a primary extension in the machine direction (MD), first 701 and second 702 faces and a first edge 703 and a second edge 704, the first and second edges 703, 704 extending in the machine direction (MD).

A first adhesive 250 is arranged on at least a portion of the first face 201 of the first web 200 or on at least the portion of the first face 301 of the second web 300. At least one discontinuous elastic thread 510 is arranged on at least the portion of the first face 201 of the first web 200 or on at least the portion of the first face 301 of the second web 300 which includes the first adhesive 250.

A second adhesive 260 is arranged on at least a portion of the first face 701 of the third web 700 or on at least a portion of the first face 301 of the second web 300. At least one discontinuous elastic thread 511 is arranged on at least the portion of the first face 701 of the third web 700 or on at least the portion of the first face 301 of the second web 300 which includes the second adhesive 260.

The third web 700 lies adjacent and substantially parallel with the first web 200, in a spaced arrangement with the first faces 201, 701 of the webs 200, 700 facing the same direction, such that the first edges 203, 703 of respective first 200 and third 700 webs are adjacent.

The first face 301 of the second web 300 overlies the first face 201 of the first web 200; the first 200 and second webs 300 being fixed together such that the at least one discontinuous elastic thread 510 is sandwiched between the first faces 201, 301 of the respective first and second webs 200, 300.

The first face 301 of the second web 300 also overlies the first face 701 of the third web 700; the third 700 and second webs 300 being fixed together such that the at least one discontinuous elastic thread 511 is sandwiched between the first faces 701, 301 of the respective third and second webs 700, 300.

The at least one discontinuous elastic thread 510 is present in a first pattern (R1). Pattern (R1) corresponds to the portion of pattern (P1), described above, which is located on the first web 200. The first pattern (R1) therefore forms loops 520 which extend from the first edge 203 of the first web 200 and back to the first edge 203 of the first web 200; so that the discontinuous elastic threads 510 terminate at each point at which they meet the first edge 203 of the first web 200.

Similarly, the at least one discontinuous thread 511 is present in a second pattern (R2). Pattern (R2) corresponds to the portion of pattern (P2), described above, which is located on the third web 700. The second pattern (R2) thus forms loops 521 which extend from the first edge 703 of the third web 700 and back to the first edge 703 of the third web 700; so that the discontinuous elastic threads 511 terminate at each point at which they meet the first edge 703 of said third web 700.

The loops 520, 521 of the patterns (R1, R2) may be curved; however, the patterns (R1, R2) can take a variety of forms, and may include one or more straight (linear) sections or variations on such patterns (R1, R2). The loops 520, 521 of the patterns (R1, R2) should have an axis of symmetry lying in the cross-direction (CD), in order for each absorbent article 10, or pant-type article 20 to have an axis of symmetry.

As shown in FIG. 1, first and second patterns (R1, R2) are synchronised such that the point in the machine direction (MD) at which the first discontinuous threads 510 are located furthest from the first edge 203 of the first web 200 corresponds substantially to the point in the machine direction (MD) at which the second discontinuous threads 511 are located furthest from the first edge 703 of the third web 700. In other words, the first and second patterns R1, R2 have the same repeat frequency and diverge at essentially the same place in the machine direction.

The method illustrated in FIG. 1 allows the elasticated web 140 to be formed. In particular, in that the elastic threads 500, 502 are secured between first and second loop retaining means 410, 411 (in particular, between the resilient belts 401, 403 and the central cylinder 620 as shown in FIG. 1) elastic threads 500, 502 are in tension, which allows accurate cutting of the elastic threads 500, 502 to be carried out, which is not possible with the methods of the prior art. Accordingly, discontinuous elastic threads 510, 511 can terminate at each point at which they meet the first edge 203 of the first web 200, or the first edge 703 of the third web 700, respectively.

Also provided is a method for manufacturing a pant-type article 20 from the elasticated web 140. The method for manufacturing pant-type articles 20 according to this embodiment is illustrated in FIG. 3.

Firstly, an elasticated web 140 is provided, according to the method of FIG. 1. The elasticated web 140 has discontinuous elastic threads 510, 511 in which at least one first discontinuous elastic thread 510 is sandwiched between the first faces 201, 301 of respective first and second webs 200, 300; and at least one second discontinuous elastic thread 511 is sandwiched between the first faces 701, 301 of respective third and second webs 700, 300. The first and second discontinuous elastic threads 510, 511 are synchronised, as described above.

A leg region 122 of the elasticated web 140, defined substantially between discontinuous elastic threads 510, 511 of the first and third webs 200, 700, is cut out, so as to form leg openings 121. Cutting the elasticated web 140 to form leg openings 121 may take place before or after the step of folding the web 140, described below. Cutting the leg region 122 out to form leg openings 121 may take place through mechanical means (e.g. blades or punches) or methods such as laser, water cutting jet, ultrasonic or thermal cutting, or combinations thereof. Use of a rotary die cutter (RDC) is a technique used in a particular embodiment.

Figure 3:
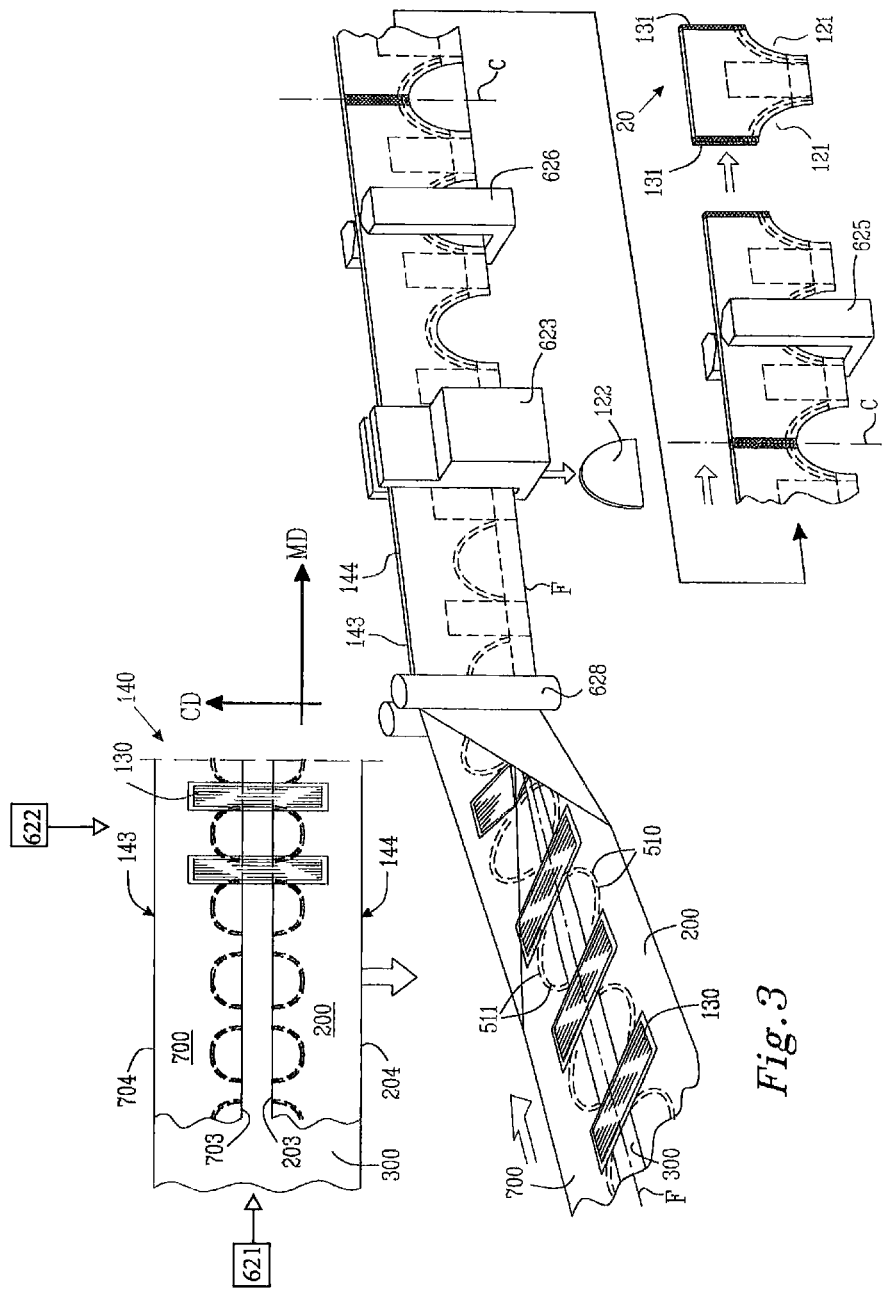
FIG. 3 shows how a pant-type article may be produced from the elasticated web made by the method of FIG. 1.
Figure 11:
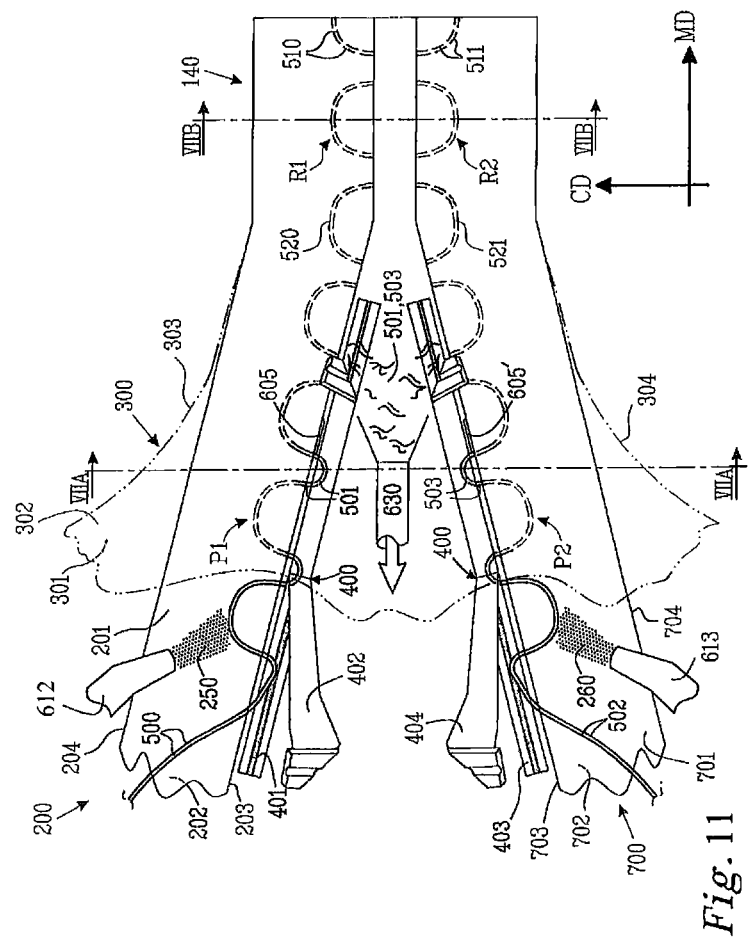
FIG. 11 is a simplified view of an embodiment of a method for manufacturing an elasticated web.
Figures 11A, 11B:
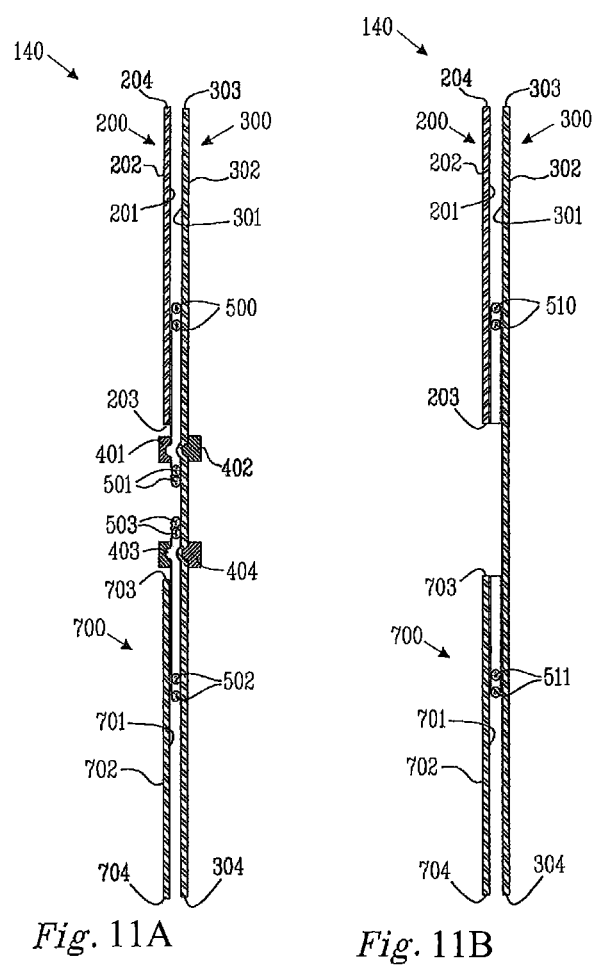
FIG. 11A is an expanded cross-sectional view along the line VIIA-VIIA in FIG. 11.
FIG. 11B is an expanded cross-sectional view along the line VIIB-VIIB in FIG. 11.
Figure 12A:
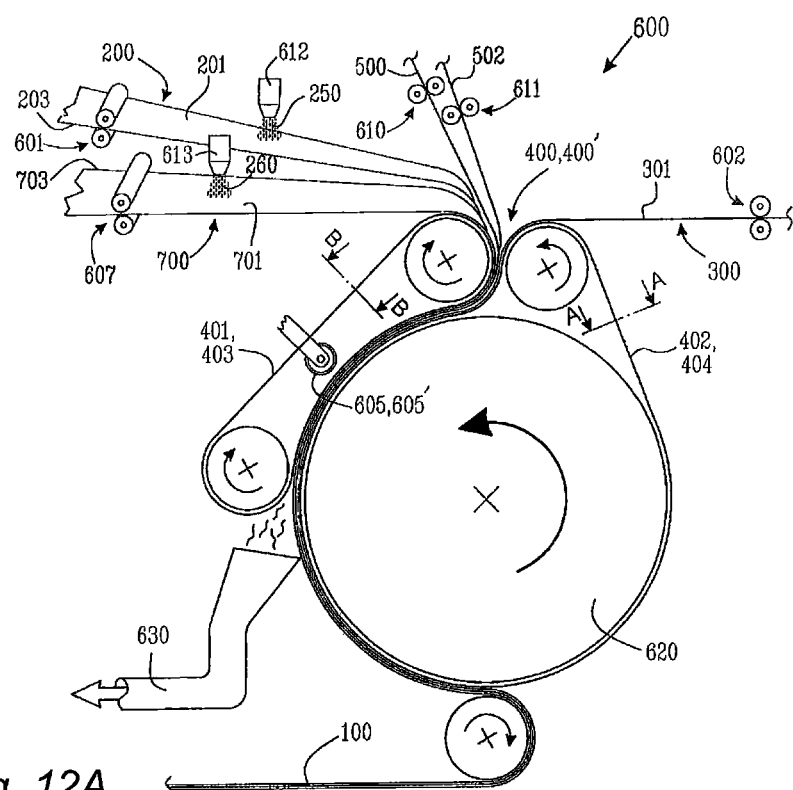
FIG. 12A is a cross-sectional view of an apparatus suitable for providing the elasticated web of the embodiment in FIGS. 11.
Figure 12B:
FIG. 12B is an expanded cross-sectional view along lines A-A and B-B in FIG. 12A.

As shown in FIG. 3, the elasticated web 140 is folded along a fold-line (F), so that first and second edges 143, 144 of the elasticated web 140 become arranged substantially adjacent one another and substantially parallel. Suitably, the elasticated web 140 is folded such that the second web 300 is located on the outside of the fold, as shown in FIG. 3. However, the opposite situation is possible, as will become evident in the discussion of FIGS. 6 and 8, below.

The folded elasticated web 140 is then joined along cutting lines (C). Cutting lines (C) extend substantially in the cross direction (CD) from the first and second edges 143, 144 of the elasticated web 140 to the fold-line (F). The cutting lines (C) are located substantially at the point at which the discontinuous elastic threads 510, 511 are located furthest from the fold-line (F). Joining the folded elasticated web 140 in this manner will eventually form side-seams 131 in the finished pant-type article 20. Joining to form side-seams 131 can take place by adhesion, thermal or ultrasonic welding or any common method known in the art.

The elasticated web 140 is then cut along cutting lines (C) such that the elasticated web (140) remains joined on either side of the cut. Individual pant-type articles (20) are thereby provided. This cutting step may take place through any cutting method described above for cutting of the leg openings 121.

If the pant-type article 20 is to include an absorbent packet 130, an absorbent packet 130 is placed so as to overlie at least a portion of the first web 200, second web 300 and/or the third web 700. The absorbent packet 130 is then fixed to at least one of the first, second and/or third webs 200, 300, 700. The absorbent packets 130 are, in particular embodiments, placed on the elasticated web 140 on the face thereof which includes the first 200 and third 700 webs. This will provide pant-type articles 20 according. to FIG. 7. Alternatively, the absorbent packets 130 are placed on the elasticated web 140 on the face thereof which includes the second web 300. This will provide pant-type articles 20 according to FIG. 8. Absorbent packets 130 are applied to the elasticated web 140 at any point before the web is folded.

The absorbent packet 130 generally includes an absorbent core 133 covered by one or more cover layers 134.

The absorbent core 133 can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbents in an absorbent body. The thin absorbent bodies, which are common in for example baby diapers and incontinence guards, often include a compressed mixed or layered structure of cellulosic fluff pulp and superabsorbent. The size and absorbent capacity of the absorbent core may be varied to be suited for different uses such as for infants or for incontinent adults. The absorbent core 133 may include one or more layers which may be selected to improve the handling of bodily waste. Such layers are designed to receive a large amount of liquid in a short space of time and distribute it evenly across the absorbent core 133. They may include so-called transfer, distribution, surge or acquisition layers.

Cover layers 134 surround the absorbent core 133, and act to maintain the integrity and shape of the absorbent core 133, and to provide good attachment to the elasticated web 140. Cover layers 134 may also provide the absorbent core 133 with appropriate liquid-handling properties, and are therefore suitably different on each face of the absorbent core 133. For example, the face of the absorbent core 133 which is to face the wearer may include a cover layer 134 which exhibits rapid liquid intake, while the cover layer 134 of the absorbent core 133 which is to face the wearer's garment may exhibit liquid-barrier properties.

Absorbent packets 130 are generally placed so as to overlap the second web 300, and fixed thereto. They may be placed so as to overlie the first 200 and third 700 webs, and fixed to both or one of the first and third webs 200, 700. The absorbent packet 130 may be applied in such a way that the side edges of the packet are located adjacent the ends of the discontinuous threads 510, 511. Fixing of the absorbent packet may be carried out using any known method, such as e.g. thermal welding, ultrasonic welding or adhesion. Adhesion is most preferred, and any suitable adhesive, such as that used as the first adhesive 250 may be used.

Depending on the design of the absorbent packet 130, and its purpose, the packet 130 can overlap first and third webs 200, 700 to the same extent, or it may overlap one of these webs to a greater extent than the other. The absorbent packet 130 is fixed in a position located equidistant from two adjacent discontinuous elastic threads 510 in the transverse direction. In particular embodiments, the absorbent packet 130 does not overlap with the discontinuous elastic threads 510, but it may do so.

Additional material layers may be added to the pant-type article 20 at any point during the above-described manufacturing process. For example, a topsheet including a nonwoven or nonwoven laminate may be added to the pant-type article 20 on the side which is intended to face the wearer's skin. A liquid-impermeable backsheet may be added to the pant-type article 20 on the side which is intended to face the wearer's garments.

The pant-type articles 20 may include additional components such as waist elastics 135, body elastics 137 and standing gathers. Suitable methods for applying such components will be known to the skilled person.

Also provided is a method for manufacturing absorbent articles 10 in the form of open diapers from the elasticated web 140 of the second embodiment. This method is illustrated schematically in FIG. 4, and includes the steps of:

providing an elasticated web 140 having discontinuous elastic threads 510, 511 in which at least one first discontinuous elastic thread 510 is sandwiched between the first faces 201, 301 of respective first and second webs 200, 300; and at least one second discontinuous elastic thread 511 is sandwiched between the first faces 701, 301 of respective third and second webs 700, 300;

placing an absorbent packet 130 so as to overlie at least a portion of the first web 200, second web 300 and/or the third web 700, and fixing the absorbent packet 130 to at least one of the first, second and/or third webs 200, 300, 700;

cutting out a leg region 122 of the elasticated web 140 defined substantially between discontinuous elastic threads 510, 511 of the first and third webs 200, 700, so as to form leg openings 121;

providing fastening means 132 on the elasticated web 140; and cutting the elasticated web 140 along cutting lines (C), the cutting lines (C) extending substantially in the cross direction (CD) from the first edge 143 to the second edge 144 of the elasticated web 140, the cutting lines (C) being located substantially at the point at which the discontinuous elastic threads 510, 511 are located furthest from the first edges 203, 703 of the first 200 and third 700 webs.

Details of individual steps of this method are the same as those described in relation to FIG. 3, above.

Fastening means 132 are components which act to fasten the absorbent article 10 in the form of an open diaper about the waist of a wearer. Fastening means 132 may include adhesive-type or hook-and-loop-type (Velcro(R)) fasteners. The absorbent articles 10 may include additional components such as waist elastics 135, body elastics 137 and standing gathers. Suitable methods for applying such components will be known to the skilled person.

It is possible that the steps of placing the absorbent packets 130, cutting out leg openings 121 and cutting the elasticated web 140 along cutting lines (C) can take place in any order. However, it is preferable that the step of cutting the elasticated web 140 along cutting lines (C) takes place last in this series, so that the integrity of the elasticated web 140 is maintained while absorbent packets 130 are fixed to it, and leg openings 121 are cut out.

Also provided is an apparatus 600 for manufacturing an elasticated web 140 having discontinuous elastic threads 510, 511 according to the embodiment illustrated in FIG. 1.

The apparatus 600 is illustrated in FIG. 2, and includes:
- first web supply means 601, for supplying the first web 200;
- second web supply means 602, for supplying the second web 300;
- third web supply means 607, for supplying the third web 700;
- first elastic thread supply means 610 for supplying the at least one first elastic thread 500;
- second elastic thread supply means 611 for supplying the at least one second elastic thread 502;
- first adhesive supply means 612 for supplying the first adhesive 250;
- second adhesive supply means 613 for supplying the second adhesive 260;
- and cutting means 605, 605' for cutting the first and second elastic threads 500, 502.

The first and second web supply means 601, 602 are as described above for the apparatus of the first embodiment. The third web supply means 607 may also be as described above for the first and second web supply means 601, 602.

The first, second and third web supply means 601, 602, 607 typically include a supply of first, second or third web 200, 300, 700 (e.g. a roll) and means adapted for feeding the first, second or third web 200, 300, 700 in the machine direction. The web supply means 601, 602, 607 may each independently include any suitable combination of cylinders, belts, rods tensioning means or the like. The first and third web supply means 601, 607 are generally arranged such that first 200 and third 700 webs run in parallel, as shown in FIG. 2.

The first adhesive supply means 612 is arranged so as to apply a first adhesive 250 to at least a portion of the first face 201 of the first web 200 or to at least a portion of the first face 301 of the second web 300.

The second adhesive supply means 613 is arranged so as to apply a second adhesive 260 to at least a portion of the first face 701 of the third web 700 or to at least a portion of the first face 301 of the second web 300.

The first and second adhesive supply means 612, 613 typically include a slot coater, roller, sprayer or similar. The adhesive supply means 612, 613 may be able to reciprocate in the cross-direction, so as to be able to apply the first and second adhesives 250, 260 to the respective web 200, 300, 700 as required, e.g. in a pattern (P). The adhesive supply means can also be divided into several crosswise sections so as to be able to apply adhesive in a pattern.

The first elastic thread supply means 610 is arranged so as to apply at least one first elastic thread 500 on at least the portion of the first face 201 of the first web 200 or on at least the portion of the first face 301 of the second web 300 which includes the first adhesive 250. The at least one first elastic thread 500 is applied in a pattern (P), the pattern (P) oscillating in the cross-direction (CD) and extending in the machine direction (MD).

The second elastic thread supply means 611 is arranged so as to apply at least one second elastic thread 502 on at least the portion of the first face 701 of the third web 700 or on at least the portion of the first face 301 of the second web 300 which includes the second adhesive 260. The at least one second elastic thread 502 is applied in a pattern (P), the pattern (P) oscillating in the cross-direction (CD) and extending in the machine direction (MD).

The first and second elastic thread supply means 610, 611 may include guide fingers, and may include elongated members which can reciprocate in the cross-direction.

The second web supply means 602 is arranged so as to apply the first face 301 of the second web 300 on the first face 201 of the first web 200 and on the first face 701 of the third web 700, as shown in FIGS. 1 and 2. First 200 and second webs 300 are fixed together; and the third 700 and the second 300 webs are fixed together; such that the at least one first elastic thread 500 is partly sandwiched between the first faces 201, 301 of respective first and second webs 200, 300; and the at least one second elastic thread 502 is partly sandwiched between the first faces 701, 301 of respective third and second webs 700, 300. Methods and means for fixing the webs 200, 300, 700 together are provided above in relation to FIG. 1. Notably, the first 250 and second 260 adhesives which are present on the first 200 and third 700 webs may be used to fix these webs to the second web 300.

The pattern (P1) is arranged such that it extends over the first edge 203 of the first web 200 to form first loops 501 in the first elastic threads 500 which project in the cross-direction CD from the first edge 203 of the first web 200. Similarly, pattern (P2) is arranged such that it extends over the first edge 703 of the third web 700 to form second loops 503 in the second elastic threads 502 which project in the cross-direction (CD) from the first edge 703 of the third web 700.

As shown in FIG. 1, first and second patterns (P1, P2) are synchronised such that the point in the machine direction (MD) at which the first elastic threads 500 are located furthest from the first edge 203 of the first web 200 corresponds substantially to the point in the machine direction (MD) at which the second elastic threads 502 are located furthest from the first edge 703 of the third web 700.

The cutting means 605, 605' is arranged so as to cut all the elastic threads 500, 502 substantially at the point at which each first elastic thread 500 crosses the first edge 203 of the first web 200 such that the first loops 501 become detached from the first web 200; and at the point at which each second elastic thread 502 crosses the first edge 703 of the third web 700; such that the second loops 503 become detached from the third web 700. Cutting should be intermittent, so as not to completely detach the second web 300 from the first web 100 or the third web 700. In other words, cuts are made only at the point at which the elastic threads 500, 502 are located.

The elastic cutting means 605, 605' is illustrated in FIGS. 1 and 2 as a rotating circular blade, although other types of cutting means may be suitable (e.g. a fixed blade, laser cutting, ultrasonic cutting). As described above, cutting could be intermittent. Intermittent cutting may be carried out by a rotating circular blade or a fixed blade, which is moved intermittently towards and away from the elastic threads 500, 502. Alternatively, intermittent cutting may be carried out by a rotating blade having raised cutting portions and recessed non-cutting portions. For intermittent cutting processes, it is important that the cutting action is synchronised, so that cutting only takes place substantially at the points at which elastic threads 500, 502 are present. It is also possible to conceive a rotating blade which cuts elastic threads 500, 502 only, but does not cut any of the webs.

The elastic cutting means 605 is arranged so as to cut all first elastic threads 500 substantially at the point at which each elastic thread 500 crosses the first edge 203 of the first web 200. Similarly, elastic cutting means 605' is arranged so as to cut all second elastic threads 502 substantially at the point at which each second elastic thread 502 crosses the first edge 703 of the third web 700. In this way, the loops 501, 503 become detached from the first and third webs 200, 700.

The apparatus 600 includes first loop retaining means 410. The first loop retaining means 410 includes at least one resilient belt 401 and at least one anvil 620. The first loop retaining means 410 is located adjacent the first edge 203 of the first web 200 and is adapted so as to secure the first loops 501 in the first loop retaining means 410. As best illustrated in FIG. 1A, the first loops 501 are secured between the resilient belt 401 and the anvil 620. In the illustrated embodiments, the anvil 620 includes a central cylinder 620, but other arrangements are possible.

The apparatus 600 also includes second loop retaining means 411. The second loop retaining means 411 includes at least one resilient belt 403 and at least one anvil 620. The second loop retaining means 411 is located adjacent the first edge 703 of the third web 700 and is adapted so as to secure the second loops 503 in the second loop retaining means 411. The second loops 503 are retained between the resilient belt 403 and the anvil 620, as illustrated in FIG. 2.

Suitably, the first and second loop retaining means 410, 411 are spaced from the first edge 203 of the first web 200, and the first edge 703 of the third web 700, respectively, so as to allow the subsequent cutting step(s) to take place.

The resilient belts 401, 402, 403, 404 which include the loop retaining means 410, 411 may be made of rubber, or any other suitable resilient material. Suitable belts can be obtained from Abatron AB, Bromma, Sweden with the tradename Correx, Beige or Polythan Gran. Suitable belts can also be obtained from Habasit AB, Hindas, Sweden, under the tradename Polycord R8. Resilient belts 401, 402, 403, 404 are typically located a distance of between 0.5 and 10 cm from the first edge 203 of the first web 200, or the first edge 703 of the third web 700.

Further details of the anvil 620 and the resilient belts are as given for the method described above.

In a development of the invention, the first loop retaining means 410 may include at least one first 401 and at least one second 402 resilient belt which are located adjacent the first edge 203 of the first web 200; and which are adapted so as to secure the first loops 501 of the first elastic thread 500 in a nip 400 between the at least one first 401 and the at least one second 402 resilient belt. Similarly, the second loop retaining means 411 may include at least one third 403 and at least one fourth 404 resilient belt which are located adjacent the first edge 703 of the third web 700; and which are adapted so as to secure the second loops 503 of the second elastic thread 502 in a nip 400' between the at least one third 403 and the at least one fourth 404 resilient belt. In particular, a single wide resilient belt may include the third resilient belt 403 and the first resilient belt 401, and a single wide resilient belt includes the fourth resilient belt 404 and the second resilient belt 402. Combinations of various numbers of resilient belts 401, 402, 403, 404 may be used.

The first and second loops 501, 503 may be secured between substantially flat surfaces of resilient belts 401, 403 and the central cylinder 620, and held in place by friction. Indeed, if a plurality of belts 401, 402, 403, 404 are present, they may all have substantially flat surfaces.

However, the resilient belts 401, 403 may be profiled such that one resilient belt engages with one or more recesses in the anvil 620 (central cylinder 620). In the case where each loop retaining means 410, 411 includes more than one resilient belt, each belt 401, 402, 403, 404 may be profiled such that one resilient belt engages with one or more recesses in the opposing resilient belt. This profiled arrangement allows close contact between the resilient belts, and allows the loops 501, 503 of the elastic threads 500, 502 to be tightly secured between the resilient belts. Variations in the profile of each resilient belt may be made by the skilled person (e.g. two protrusions on one belt which engage with two recesses in the opposing cylinder or belt, or a belt which has a cross-section (e.g circular, semi-circular, triangular etc.), allowing it to engage with a recess in the anvil 620 or resilient belt). Alternatively, or additionally, to having recesses/protrusions, the belts 401, 402, 403, 404 may include high-friction surfaces which grip the loops 501, 503 securely.

In the embodiment illustrated in FIG. 2, first web 200, second web 300, third web 700, elastic threads 500, 502 and resilient belts 401, 403 are brought together in a single nip 400, thereby fixing these components together in a convenient and effective manner.

As is also illustrated in FIG. 2, first web supply means 601, second web supply means 602, third web supply means 607, first elastic thread supply means 610, second elastic thread supply means 611 first adhesive supply means 612, second adhesive supply means 613, cutting means 605, 605', at least one first 401, at least one second 402, at least one third 403 and at least one fourth 404 resilient belts are suitably arranged peripherally about a single central cylinder 620. However, other arrangements of these components are possible (e.g. linear). In addition, the anvil 620 may be comprised of two or more cylinders against which the elasticated web 140 is manufactured.

The apparatus 600 described above may include additional components, making it suitable for manufacturing pant-type articles 20. In this case, the apparatus 600 is illustrated schematically in FIG. 3, and additionally includes;

elasticated web supply means 621; for supply of the elasticated web 140;

optionally, absorbent packet supply means 622, for supply of absorbent packets 130 leg region cutting means 623, for cutting out leg regions 122 folding means 628 for folding the elasticated web 140 joining means 626 for joining the elasticated web 140.

elasticated web cutting means 625, for cutting elasticated web 140

The elasticated web supply means 621 is arranged so as to provide an elasticated web 140 having discontinuous elastic threads 510, 511 in which at least one first discontinuous elastic thread 510 is sandwiched between the first faces 201, 301 of respective first and second webs 200, 300; and at least one second discontinuous elastic thread 511 is sandwiched between the first faces 701, 301 of respective third and second webs 700, 300. The elasticated web supply means 621 may feed elasticated web 140 directly from the apparatus illustrated in FIG. 2; alternatively elasticated web 140 may be fed from another supply e.g. a roll. As for the first web supply means 601 described above, the elasticated web supply means 621 typically includes a supply of elasticated web 140 (e.g. a roll) and means adapted for feeding the elasticated web 140 in a machine direction. The elasticated web supply means 621 may include any suitable combination of cylinders, belts, rods or the like. The elasticated web supply means 621 may include means for controlling forces in the edges 143, 144 of the elasticated web 140, which may arise from the elastic threads 510, 511.

If required, absorbent packet supply means 622 is arranged so as to place an absorbent packet 130 such that it overlies at least a portion of the first web 200, second web 300 and/or the third web 700. The absorbent packet 130 is then fixed to at least one of the first, second and/or third webs 200, 300, 700. The absorbent packets 130 are placed on the elasticated web 140, preferably on the face thereof which includes first 200 and third 700 webs. Details of the absorbent packet 130 are to be found above. Absorbent packets 130 are applied to the elasticated web 140 at any point before the web is folded. The absorbent packet supply means 622 typically includes a supply of absorbent packets 130 (e.g. a stack or roll) any suitable combination of cylinders, belts, rods or the like arranged so as to feed the absorbent packets 130 onto the first, second and/or third webs 200, 300, 700. Suitably, the absorbent packet 130 is fixed to at least the second web 300. Fixing of the absorbent packet 130 may be carried out using any known method, such as e.g. thermal welding, ultrasonic welding or adhesion. Adhesion is most preferred, and any suitable adhesive such as that used as the first adhesive 250 may be used.

The leg region cutting means 623 is arranged so as to cut out a region of the elasticated web 140 defined substantially between discontinuous elastic threads 510, 511 of the first and third webs 200, 700, so as to form leg openings 121. The skilled person will be able to select a suitable size, location and shape for the leg openings 121 in the elasticated web 140. Leg region cutting means 623 may include mechanical means (e.g. blades or punches) or other cutting means such as lasers, ultrasonic or thermal cutting means, rotary die cutters or combinations thereof. Leg region cutting means 623 may be arranged before or after absorbent packet supply means 622 in the apparatus 600. Equally, leg region cutting means 623 may be arranged before or after folding means 628.

Folding means 628 is arranged so as to fold the elasticated web 140 along a fold-line (F). The fold-line (F) runs in the machine direction of the elasticated web 140. First and second edges 143, 144 of the elasticated web 140 become arranged substantially adjacent one another and substantially parallel. The second web 300 is preferably located on the outside of the fold, but may even be located on the inside of the fold. If an absorbent packet 130 is present, it is located on the inside of the fold. Folding means 617 may include any suitable combination of reciprocating or rotating members (e.g. arms or drums) webguides (e.g. metal sheets or rods), belts or the like.

The joining means 626 are arranged so as to join the folded elasticated web 140 along lines C. Lines C extend substantially in the cross direction CD from the first and second edges 143, 144 of the elasticated web 140 to the fold-line F, the cutting lines C being located substantially at the point at which the discontinuous elastic threads 510, 511 are located furthest from the fold-line F. Joining along cutting lines C will form side-seams 131 in the pant-type article. Joining can take place by adhesion, thermal or ultrasonic welding or any common method known in the art.

Elasticated web cutting means 625 is arranged so as to cut the elasticated web 140 along cutting lines (C) such that the elasticated web 140 remains joined on either side of the cut. In this way, individual pant-type articles 20 are separated from the elasticated web 140.

As described above in relation to the first embodiment, the pant-type articles 20 of the invention may include additional components such as waist elastics 135, body elastics 137 and standing gathers. Suitable methods and means for applying such components will be known to the skilled person.

The invention also provides an apparatus for manufacturing an absorbent article 10 in the form of an open diaper from the elasticated web 140.

In this case, the apparatus 600 additionally includes;
elasticated web supply means 621; for supply of the elasticated web 140;
absorbent packet supply means 622, for supply of absorbent packets 130
leg region cutting means 623, for cutting out leg regions 122
elasticated web cutting means 625, for cutting elasticated web 140 and
fastening supply means 627 for supply of fastening means 132.

Details of these components are the same as those described in relation to FIG. 3, above.

As before, the elasticated web supply means 621 is arranged so as to provide an elasticated web 140 having discontinuous elastic threads 510, 511 in which at least one first discontinuous elastic thread 510 is sandwiched between the first faces 201, 301 of respective first and second webs 200, 300; and at least one second discontinuous elastic thread 511 is sandwiched between the first faces 701, 301 of respective third and second webs 700, 300.

The (optional) absorbent packet supply means 622 are arranged so as to place an absorbent packet 130 so as to overlie at least a portion of the first web 200, second web 300 and/or the third web 700, and to fix the absorbent packet 130 to at least one of the first, second and third webs 200, 300, 700.

The leg region cutting means 623 is arranged so as to cut out a region of the elasticated web 140 defined substantially between discontinuous elastic threads 510, 511 of the first and third webs 200, 700, so as to form leg openings 121. The elasticated web cutting means 625 is arranged so as to cut the elasticated web 140 along cutting lines C, the cutting lines (C) extending substantially in the cross direction (CD) from the first edge 143 to the second edge 144 of the elasticated web 140, the cutting lines (C) located substantially at the point at which the discontinuous elastic threads 510, 511 are located furthest from the first edges 203, 703 of the first 200 and third 700 webs. The fastening supply means 627 is arranged so as to provide fastening means 132 on the elasticated web 140. The fastening means 132 are suitably located on the outside face of the absorbent article 10. Fastening supply means 627 includes a supply of fastening means 132 (e.g. a roll or stack) and means for feeding them to the nascent absorbent article 10 (e.g. nips, cylinders or belts) and means for joining the fastening means 132 to the article 10. Fastening means 132 may be joined to the absorbent article 10 by means of welding or gluing. Fastening means 132 are discussed in more detail above.

As described above, the pant-type articles 20 of the invention may include additional components such as waist elastics 135, body elastics 137 and standing gathers. Suitable methods and means for applying such components will be known to the skilled person.

Various pant-type articles 20 which are produced according to the methods described herein are illustrated in FIGS. 5-8. FIGS. 5A-8A are expanded cross-sectional views through the perspective view of FIGS. 5-8 taken along the longitudinal centre line (A-A) in each case.

Each of the pant-type articles 20 illustrated in FIGS. 5-8, include a front panel 150 and a rear panel 160. The front panel is that portion of the article 10 which—when the article is in use—is intended to cover at least a portion of the groin and/or lower belly of the wearer. The rear panel is that portion of the article 20 which—when the article is in use—is intended to cover at least a portion of the buttocks and/or lower back of the wearer.

The illustrated pant-type articles 20 also include a crotch panel 181 which extends between the front panel 150 and the rear panel 160 in the longitudinal direction (L) of the pant-type article 20 and is joined to the front and rear panels 150, 160. The crotch panel 181 is that portion of the article 10 which—when the article is in use—lies substantially between the legs of the wearer.

The crotch panel 181 includes a crotch layer 180 and/or an absorbent packet 130. The pant-type articles of FIGS. 7-8 include various combinations of crotch layer 180 and absorbent packet 130. The absorbent packet 130 is as described above, and generally includes an absorbent core 133 covered by one or more cover layers 134.

The front and rear panels 150, 160 of the pant-type articles 20 of FIGS. 5-8 are joined to each other at side seams 131 located at the transverse edges thereof.

As shown in FIGS. 5-8, and most clearly in FIGS. 5A, 6A, 7A and 8A, at least the front panel 150 of each embodied pant-type article 20 includes a first front layer 151, a second front layer 152 and at least two first leg elastics 153 located between the first 151 and second 152 front layers. The first front layer 151 corresponds to the first web 200 used in the methods described above, and may therefore include any material suitable for the first web 200. The second front layer 152 corresponds to the second web 300 used in the methods described above, and may therefore include any material suitable for the second web 300.

The at least two first leg elastics 153 are located symmetrically on either side of a longitudinal centre line (L1) of the pant-type article 20. The first leg elastics 153 are adapted to seal the leg openings 121 against the legs of the wearer. The first leg elastics 153 correspond to the first discontinuous elastic threads 510 in the method described above, and may therefore include any material suitable for such threads. The at least two first leg elastics 153 are located on either side of a longitudinal centre line (L1) of the pant-type article 20.

The first front layer 151 is defined by first 154 and second edges 155 which extend substantially in the transverse direction (T) of the pant-type article 20. These first 154 and second edges 155 of the first front layer 151 correspond to the first 203 and second 204 edges of the first web 200 used in the methods of the invention. The first edge 154 is that edge which is located closest to the crotch panel 181 of the pant-type article 20.

The rear panel 160 of the pant-type articles 20 of FIGS. 5-8 also includes a first rear layer 161, a second rear layer 162 and at least two second leg elastics 163 located between the first 161 and second 162 rear layers. The at least two second leg elastics 163 are located on either side of longitudinal centre line (L1) of the pant-type article 20.

The first rear layer 161 corresponds to the third web 700 used in the method described above, and may therefore include any material suitable for the third web 700. The second rear layer 162 corresponds to the second web 300 used in the methods described above, and may therefore include any material suitable for the second web 300.

The second leg elastics 163 correspond to the second discontinuous elastic threads 511 in the method described above, and may therefore include any material suitable for such threads.

FIGS. 5-8 show pant-type articles 20 having pairs of elastic threads 153, 163; however, it is also conceivable that a lesser or greater number of elastic threads 153, 163 are included. In particular, it is useful to have more elastic threads 163 in the rear panel 160.

The first rear layer 161 is defined by first 164 and second edges 165 which extend substantially in the transverse direction (T) of the pant-type article 20. These first 164 and second edges 165 of the first rear layer 161 correspond to the first 703 and second 704 edges of the third web 700 used in the methods of the invention. The first edge 164 is that which is located closest to the crotch panel 181 of the pant-type article 20.

Common to all pant-type articles 20 of FIGS. 5-8 is that the first leg elastics 153 in the front panel 150 terminate at the point at which they meet the first edge 154 of the first front layer 151, and that the second leg elastics 163 in the rear panel 160 terminate at the point at which they meet the first edge 164 of the first rear layer 161. Typically, the leg elastics 153, 163 extend from the first edge 154, 164 of the first front or rear layer 151, 161 towards the side seams 131 of the article 20. The leg elastics 153, 163 are typically curved.

Suitably, the leg elastics 153, 163 do not overlap the absorbent packet 130 at all. It is therefore preferred that the at least two first leg elastics 153 and the at least two second leg elastics 163 are located on either side of the absorbent packet 130 of the pant-type article 20 in the transverse direction (T).

FIGS. 5 and 5A show a pant-type article 20 with a single second layer 170 which does not include an absorbent packet 130, and in which the single second layer 170 lies towards the outside of the product. FIGS. 6 and 6A show a pant-type article 20 with a single second layer 170 which does not include an absorbent packet 130, and in which the single second layer 170 lies towards the inside of the product. Whether articles of FIGS. 5 or FIG. 6 are made depends on which way the elasticated web 140 is folded during manufacture of the pant-type articles 20.

FIGS. 7 and 7A show a pant-type article 20 with a single second layer 170, and which includes an absorbent packet 130, in which the single second layer 170 lies towards the outside of the product. FIGS. 8 and 8A show a pant-type article 20 with a single second layer 170, and which includes an absorbent packet 130, in which the single second layer 170 lies towards the inside of the product. Whether articles of FIG. 7 or FIG. 8 are made depends on which face the absorbent packet 130 is applied to the elasticated web 140 during manufacture.

The pant-type articles 20 of the invention may include additional components such as waist elastics 135, body elastics 137 and standing gathers.

FIGS. 9 and 10 show absorbent articles 10 in the form of open diapers. FIGS. 9A and 10A are cross-sectional views along the longitudinal centre lines (A-A) in FIGS. 9 and 10, respectively.

The absorbent articles 10 illustrated extend in the longitudinal (L) and transverse (T) directions, as shown.

Each of the absorbent articles 10 illustrated in FIGS. 9-10 includes a front panel 150 and a rear panel 160 and an absorbent packet 130. Each article also includes a crotch panel 181. The crotch panel 181 extends between the front panel 150 and the rear panel 160 in the longitudinal direction (L) of the absorbent article 10 and is joined to the front and rear panels 150, 160. The crotch panel 181 includes an absorbent packet 130 and optionally, a crotch layer 180.

At least one of the front and rear panels 150, 160 include fastening means 132. Suitable fastening means 132, and means and methods for their application are discussed above.

At least the front panel 150 includes a first front layer 151, a second front layer 152 and at least two first leg elastics 153 located between the first 151 and second 152 front layers. The at least two first leg elastics 153 are located on either side of a longitudinal centre line L1 of the absorbent article 10.

The first front layer 151 is defined by first 154 and second edges 155 which extend substantially in the transverse direction T of the absorbent article 10. The first 154 edge is that which is located closest to the crotch panel 181 of the absorbent article 10.

The rear panel 160 also includes a first rear layer 161, a second rear layer 162 and at least two second leg elastics 163 located between the first 161 and second 162 rear layers. The at least two second leg elastics 163 are located on either side of longitudinal centre line L1 of the absorbent article 10.

FIGS. 9-10 show absorbent articles 10 having pairs of elastic threads 153, 163; however, it is also conceivable that a lesser or greater number of elastic threads 153, 163 are included. In particular, it is useful to have more elastic threads 163 in the rear panel 160.

The first rear layer 161 is defined by first 164 and second edges 165 which extend substantially in the transverse direction T of the absorbent article 10. The first 164 edge is that which is located closest to the crotch panel 181 of the absorbent article 10.

Suitable materials for the layers 151, 152, 161, 162, absorbent packet 130 and the elastics 153, 163 are provided above for the pant-type articles 20 of the invention.

As shown in FIGS. 9-10, the first leg elastics 153 in the front panel 150 terminate at the point at which they meet the first edge 154 of the first front layer 151 while the second leg elastics 163 in the rear panel 160 terminate at the point at which they meet the first edge 164 of the first rear layer 161.

Suitably, the leg elastics 153, 163 do not overlap the absorbent packet 130 at all. It is therefore preferred that the at least two first leg elastics 153 and the at least two second leg elastics 163 are located on either side of the absorbent packet 130 of the absorbent article 10 in the transverse direction (T).

In the articles illustrated in FIGS. 9 and 10, a single second layer 170 includes the second front layer 152, the second rear layer 162 and the crotch layer 180. The single second layer 170 are therefore derived from the second web 300 of the method described above, while first front layer 151 and first rear layer 161 are derived from the first web 200 and second web 300 of the above method.

FIG. 9 shows an absorbent article 10 in which the absorbent packet 130 is located on the first 200 and third 700 webs during manufacture. The second web 300 (=single second layer 170) therefore lies on the face of the absorbent article 10 opposite to the absorbent packet 130. This arrangement provides the absorbent article 10 with a continuous outer face, comprised of the single second layer 170/second web 300.

FIG. 10 shows an absorbent article 10 in which the absorbent packet 130 is located on the second web 300 during manufacture. The second web 300 (=single second layer 170) therefore lies on the same face of the absorbent article 10 as the absorbent packet 130.

FIG. 9A is an expanded cross-sectional view along the line IXA-IXA in FIG. 9; i.e. through the absorbent article 10 along its length. FIG. 10A is an expanded cross-sectional view along the line XA-XA in FIG. 10; i.e. through the absorbent article 10 along its length.

The absorbent articles 10 of the invention may include additional components such as waist elastics 135, body elastics 137 and standing gathers.

The invention has been described with reference to a number of embodiments. However, the scope of the invention should not be considered as limited to the illustrated and described embodiments. Instead, features from certain embodiments may be combined at will with features from other embodiments, while remaining within the scope of the claims. The scope of the invention should be determined by the appended claims.

The invention claimed is:

1. A method for manufacturing an elasticated web having discontinuous elastic threads, said method comprising the steps of;
   a. providing a first web, said first web having a primary extension in the machine direction, first and second faces and a first edge and a second edge, said first and second edges extending in the machine direction;
   b. providing a second web, said second web also having a primary extension in the machine direction, first and second faces and a first edge and a second edge, said first and second edges extending in the machine direction;
   c. providing a third web said third web having a primary extension in the machine direction, first and second faces and a first edge and a second edge, said first and second edges extending in the machine direction;
   d. arranging said third web to lie adjacent and substantially parallel with said first web, in a spaced arrangement with the first faces of said webs facing the same direction, such that the first edges of the respective first and third webs are adjacent;
   e. applying a first adhesive to at least a portion of the first face of said first web or to at least a portion of the first face of the second web;
   f. applying a second adhesive to at least a portion of the first face of said third web or to at least a portion of the first face of the second web;
   g. applying at least one first elastic thread on at least the portion of said first face of said first web or on at least the portion of said first face of said second web which comprises said first adhesive; wherein said at least one first thread is applied in a first pattern, said first pattern oscillating in the cross-direction and extending in the machine direction,
   h. applying at least one second elastic thread on at least the portion of said first face of said third web or to at least the portion of said first face of said second web which comprises said second adhesive; wherein said at least one second elastic thread is applied in a second pattern, said second pattern oscillating in the cross-direction and extending in the machine direction,
   i. applying a portion of the first face of said second web on the first face of said first web, and fixing said first and second webs together such that said at least one first elastic thread is partly sandwiched between the first faces of the respective first and second webs; such that the first pattern extends over the first edge of the first web to form first loops in said first elastic thread which project in the cross-direction from said first edge of said first web;
   j. applying a portion of the first face of said second web on the first face of said third web, and fixing said third and second webs together such that said at least one second elastic thread is partly sandwiched between the first faces of the respective second and third webs; such that the second pattern extends over the first edge of the third web to form second loops in said second elastic thread which project in the cross-direction from said first edge of said third web; and such that said first and second patterns are synchronised such that the point in the machine direction at which the first elastic threads are located furthest from the first edge of the first web corresponds substantially to the point in the machine direction at which the second elastic threads are located furthest from the first edge of the third web;
   k. securing the first loops of said first elastic threads in a first loop retaining element comprising at least one resilient belt or belt portion and at least one anvil, said loop retaining element being located adjacent the first edge of said first web;
   l. securing the second loops of said second elastic threads in a second loop retaining element comprising at least one resilient belt or belt portion and at least one anvil, said second loop retaining element being located adjacent the first edge of said third web;
   m. cutting all the first elastic threads substantially at the point at which each first elastic thread crosses the first edge of said first web such that the loops become detached from the first web;

n. cutting all the second elastic threads substantially at the point at which each second elastic thread crosses the first edge of said third web such that the loops become detached from the third web;

wherein step d. can take place at any point in the process before step i. so as to provide the elasticated web having discontinuous elastic threads.

2. The method according to claim 1, wherein steps e.-l. of the method occur substantially simultaneously in a single nip.

3. The method according to claim 1, wherein the resilient belt portion of the first loop retaining element and the resilient belt portion of the second loop retaining element are comprised by a single wide resilient belt.

4. The method according to claim 1, wherein the first loop retaining element comprises at least one first resilient belt or belt portion and at least one second resilient belt or belt portion which are located adjacent the first edge of said first web and/or the second loop retaining element comprises at least one third resilient belt or belt portion and at least one fourth resilient belt or belt portion which are located adjacent the first edge of said third web.

5. The method according to claim 4, wherein a single wide resilient belt comprises the third resilient belt portion and the first resilient belt portion, and a single wide resilient belt comprises the fourth resilient belt portion and the second resilient belt portion.

6. The method according to claim 1, wherein the at least one anvil is a central cylinder.

7. A method for manufacturing pant-type articles, said method comprising the steps of:

a. carrying out the method according to claim 1 to provide the elasticated web having discontinuous elastic threads in which at least one first discontinuous elastic thread is sandwiched between the first faces of the respective first and second webs; and at least one second discontinuous elastic thread is sandwiched between the first faces of the respective third and second webs, said elasticated web having first and second edges extending in the machine direction;

b. cutting out a leg region of the elasticated web defined substantially between discontinuous elastic threads of the first and third webs so as to form leg openings;

c. folding the elasticated web along a fold-line, so that the first and second edges of the elasticated web become arranged substantially adjacent one another and substantially parallel, d. joining the folded elasticated web along cutting lines, said cutting lines extending substantially in the cross-direction from the first and second edges of the elasticated web to the fold-line, said cutting lines being located substantially at the point at which the discontinuous elastic threads are located furthest from the fold-line; to form side-seams;

e. cutting the elasticated web along cutting lines such that the elasticated web remains joined on either side of the cut;

wherein steps b. and c. can take place in any order, so as to thereby provide pant-type articles.

8. The method according to claim 7, said method comprising the additional step of placing an absorbent packet so as to overlie at least a portion of at least one of the first web, the second web or the third web, and fixing said absorbent packet to at least one of said first, second or third webs; after step a., but before step c.

9. A method for manufacturing absorbent articles, said method comprising the steps of;

a. carrying out the method according to claim 1 to provide the elasticated web having discontinuous elastic threads in which at least one first discontinuous elastic thread is sandwiched between the first faces of the respective first and second webs; and at least one second discontinuous elastic thread is sandwiched between the first faces of the respective third and second webs, said elasticated web having first and second edges extending in the machine direction;

b. placing an absorbent packet so as to overlie at least a portion of at least one of the first web, the second web or the third web, and fixing said absorbent packet to at least one of said first, second or third webs;

c. cutting out a region of the elasticated web defined substantially between the discontinuous elastic threads of the first and third webs, so as to form leg openings;

d. providing a fastening element on said elasticated web;

e. cutting the elasticated web along cutting lines, said cutting lines extending substantially in the cross-direction from the first edge to the second edge of the elasticated web, said cutting lines being located substantially at the point at which the discontinuous elastic threads are located furthest from the first edges of the first and third webs; so as to provide absorbent articles.

10. An apparatus for carrying out the method according to claim 1, said apparatus comprising:

first web supply element for supplying said first web;
second web supply element for supplying said second web;
third web supply element for supplying said third web;
first elastic thread supply element for supplying said at least one first elastic thread;
second elastic thread supply element for supplying said at least one second elastic thread;
first adhesive supply element for supplying said first adhesive;
second adhesive supply element for supplying said second adhesive;
cutting element for cutting said first and second elastic threads;

wherein said first adhesive supply element is arranged so as to apply the first adhesive to at least a portion of the first face of said first web or to at least a portion of the first face of the second web;

wherein said first elastic thread supply element is arranged so as to apply the at least one first elastic thread on at least the portion of said first face of said first web or on at least the portion of said first face of said second web which comprises said first adhesive; wherein said at least one first elastic thread is applied in the first pattern, said first pattern oscillating in the cross-direction and extending in the machine direction, wherein said second adhesive supply element is arranged so as to apply the second adhesive to at least a portion of the first face of the third web or to at least a portion of the first face of the second web;

wherein said second elastic thread supply element is arranged so as to apply the at least one second elastic thread on at least the portion of said first face of said third web or on at least the portion of said first face of said second web which comprises said second adhesive; wherein said at least one second elastic thread is applied in the second pattern, said second pattern oscillating in the cross-direction and extending in the machine direction, wherein said second web supply element is arranged so as to apply the first face of said second web on the first face of said first web and the first face of said third web, and fix said first and second webs together; and said third and said second webs together; such that said at least one first elastic thread is partly sandwiched between the first faces of the respective first and second webs; and said at least one second elastic thread is partly sandwiched between the first faces of the respective third and second webs; and such that the first pattern extends over the first edge of the first web to form the first loops in said first elastic threads which project in the cross-direction from said first edge of said first web; and such that the second pattern extends over the first edge of the third web to form the second loops in said second elastic threads which project in the cross-direction from said first edge of said third web; and such that said first and second patterns are synchronised such that the point in the machine direction at which the first elastic threads are located furthest from the first edge of the first web corresponds substantially to the point in the machine direction at which the second elastic threads are located furthest from the first edge of the third web;

wherein said cutting element is arranged so as to cut all the elastic threads substantially at the point at which each first elastic thread crosses the first edge of said first web such that the first loops become detached from the first web; and at the point at which each second elastic thread crosses the first edge of said third web; such that the second loops become detached from the third web; and wherein the apparatus comprises the first loop retaining element comprising at least one resilient belt and at least one anvil, said first loop retaining element located adjacent the first edge of said first web and being adapted so as to secure the first loops in said first loop retaining element and the second loop retaining element comprising at least one resilient belt and at least one anvil, said loop retaining element being located adjacent the first edge of said third web and being adapted so as to secure the second loops in said second loop retaining element.

11. The apparatus according to claim 10, in which said first, second and third webs are fixed together in a single nip.

12. The apparatus according to claim 10, wherein said first loop retaining element comprises at least one first resilient belt or belt portion and at least one second resilient belt or belt portion which are located adjacent the first edge of said first web; and which are adapted so as to secure the first loops of the first elastic thread in a nip between at least one of said at least one first and said at least one second resilient belt or belt portion or said second loop retaining element comprises at least one third resilient belt or belt portion and at least one fourth resilient belt or belt portion which are located adjacent the first edge of said third web; and which are adapted so as to secure the second loops of the second elastic thread in a nip between said at least one third and said at least one fourth resilient belt or belt portion.

13. The apparatus according to claim 12, wherein a single wide resilient belt comprises the third resilient belt portion and the first resilient belt portion, and a single wide resilient belt comprises the fourth resilient belt portion and the second resilient belt portion.

14. The apparatus according to claim 10, wherein
the first web supply element for supplying said first web;
the second web supply element for supplying said second web;
the third web supply element for supplying said third web;
the first elastic thread supply element for supplying said at least one first elastic thread;
the second elastic thread supply element for supplying said at least one second elastic thread;
the first adhesive supply element for supplying said first adhesive;
the second adhesive supply element for supplying said second adhesive;
the cutting element for cutting said first and second elastic threads; and
the first and second loop retaining elements;
are arranged peripherally about a single central cylinder.

15. The apparatus according to claim 10, said apparatus additionally comprising;
an elasticated web supply element for supply of said elasticated web having first and second edges extending in the machine direction;
optionally, an absorbent packet supply element for supply of absorbent packets;
a leg region cutting element for cutting out leg regions;
a folding element for folding the elasticated web;
a joining element for joining the elasticated web; and
an elasticated web cutting element for cutting the elasticated web wherein said elasticated web supply element is arranged so as to provide the elasticated web having discontinuous elastic threads in which at least one first discontinuous elastic thread is sandwiched between the first faces of the respective first and second webs; and at least one second discontinuous elastic thread is sandwiched between the first faces of the respective third and second webs;

wherein said absorbent packet supply element is arranged so as to place the absorbent packet so as to overlie at least a portion of at least one of the first web, the second web, or the third web, and to fix said absorbent packet to at least one of said first, second and third webs;

wherein said leg region cutting element is arranged so as to cut out the leg region of the elasticated web defined substantially between the discontinuous elastic threads of the first and third webs, so as to form leg openings;

wherein said folding element is arranged so as to fold the elasticated web along a fold-line, so that the first and second edges of the elasticated web become arranged substantially adjacent one another and substantially parallel, wherein said joining element is arranged so as to join the folded elasticated web along cutting lines, said cutting lines extending substantially in the cross-direction from the first and second edges of the elasticated web to the fold-line, said cutting lines being located substantially at the point at which the discontinuous elastic threads are located furthest from the fold-line; to form side-seams;

wherein said elasticated web cutting element being arranged so as to cut the elasticated web along the cutting lines such that the elasticated web remains joined on either side of the cut.

16. The apparatus according to claim 10, said apparatus additionally comprising:
an elasticated web supply element for supply of said elasticated web having first and second edges extending in the machine direction;
an absorbent packet supply element for supply of absorbent packets;
a leg region cutting element for cutting out leg regions;
an elasticated web cutting element for cutting the elasticated web;

a fastening supply element for supply of the fastening element;

wherein said elasticated web supply element is arranged so as to provide the elasticated web having discontinuous elastic threads in which at least one first discontinuous elastic thread is sandwiched between the first faces of the respective first and second webs; and at least one second discontinuous elastic thread is sandwiched between the first faces of the respective third and second webs;

wherein said absorbent packet supply element is arranged so as to place the absorbent packet so as to overlie at least a portion of at least one of the first web, the second web, or the third web, and to fix said absorbent packet to at least one of said first, second and third webs;

wherein said leg region cutting element is arranged so as to cut out the leg region of the elasticated web defined substantially between the discontinuous elastic threads of the first and third webs, so as to form leg openings;

wherein said fastening supply element is arranged so as to provide the fastening element on said elasticated web;

wherein said elasticated web cutting element is arranged so as to cut the elasticated web along cutting lines, said cutting lines extending substantially in the cross-direction from the first edge to the second edge of the elasticated web, said cutting lines being located substantially at the point at which the discontinuous elastic threads are located furthest from the first edges of the first and third webs.

17. The apparatus according to claim 10, wherein the at least one anvil is a central cylinder.

* * * * *